US011275086B2

(12) United States Patent
Mariani et al.

(10) Patent No.: US 11,275,086 B2
(45) Date of Patent: Mar. 15, 2022

(54) **USE OF AMINO ACID SEQUENCES FROM *MYCOBACTERIUM TUBERCULOSIS* OR CORRESPONDING NUCLEIC ACIDS FOR DIAGNOSIS AND PREVENTION OF TUBERCULAR INFECTION, DIAGNOSTIC KIT AND VACCINE THEREFROM**

(71) Applicant: Cellestis Limited, Chadstone (AU)

(72) Inventors: Francesca Mariani, Rome (IT); Massimo Amicosante, Rome (IT); Vittorio Colizzi, Rome (IT); Cesare Saltini, Grottaferrata (IT)

(73) Assignee: Cellestis Limited, Chadstone (AU)

( * ) Notice: Subject to any disclaimer, the term of this patent is extended or adjusted under 35 U.S.C. 154(b) by 0 days.

(21) Appl. No.: 16/999,727

(22) Filed: Aug. 21, 2020

(65) Prior Publication Data

US 2020/0386755 A1  Dec. 10, 2020

Related U.S. Application Data

(62) Division of application No. 16/557,536, filed on Aug. 30, 2019, now Pat. No. 10,788,491, which is a division of application No. 15/793,746, filed on Oct. 25, 2017, now Pat. No. 10,408,833, which is a division of application No. 14/798,241, filed on Jul. 13, 2015, now Pat. No. 9,829,490, which is a division of application No. 13/811,906, filed as application No. PCT/IT2011/000266 on Jul. 25, 2011, now Pat. No. 9,110,061.

(30) Foreign Application Priority Data

Jul. 23, 2010 (IT) .......................... RM2010A000411

(51) Int. Cl.
*G01N 33/569* (2006.01)
*A61K 38/10* (2006.01)
*C07K 14/35* (2006.01)
*G01N 33/68* (2006.01)
*A61K 38/16* (2006.01)
*C07K 7/08* (2006.01)

(52) U.S. Cl.
CPC ....... *G01N 33/56972* (2013.01); *A61K 38/10* (2013.01); *A61K 38/164* (2013.01); *C07K 7/08* (2013.01); *C07K 14/35* (2013.01); *G01N 33/5695* (2013.01); *G01N 33/6866* (2013.01); *G01N 2333/35* (2013.01); *G01N 2333/57* (2013.01)

(58) Field of Classification Search
None
See application file for complete search history.

(56) References Cited

U.S. PATENT DOCUMENTS

2006/0115847 A1  6/2006 Andersen et al.
2006/0182685 A1  8/2006 Bishai et al.

FOREIGN PATENT DOCUMENTS

WO        02/44406 A2   6/2002
WO    2005/021790 A2   3/2005

OTHER PUBLICATIONS

"Anergy Skin Testing and Preventive Therapy for HIV-Infected Persons: Revised Recommendations," Center for Disease Control, Recommendations and Reports 46(RR15):1-10, Sep. 5, 1997, retrieved from URL=http://www.cdc.gov/mmwr/preview/mmwrhtml/00049386.htm, on Mar. 18, 2013, 11 pages.

Bellete et al., "Evaluation of a Whole-Blood Interferon-γ Release Assay for the Detection of *Mycobacterium tuberculosis* Infection in 2 Study Populations," *Clinical Infectious Diseases* 34:1449-1456, 2002.

Chapman et al., "Rapid detection of active and latent tuberculosis infection in HIV-positive individuals by enumeration of *Mycobacterium tuberculosis*-specific T cells," *AIDS* 16:2285-2293, 2002.

De Groot et al., "From genome to vaccine: in silico predictions, ex vivo verification," *Vaccine* 19:4385-4395, 2001.

Doherty et al., "Immune Responses to the *Mycobacterium tuberculosis*-Specific Antigen ESAT-6 Signal Subclinical Infection among Contacts of Tuberculosis Patients," *Journal of Clinical Microbiology* 40(2): 704-706, Feb. 2002.

Harboe et al., "Evidence for occurrence of the ESAT-6 protein in *Mycobacterium tuberculosis* and virulent *Mycobacterium bovis* and for its absence in *Mycobacterium bovis* BCG," *Infect. Immun.* 64(1):16-22, 1996.

Lalvani et al., "Enhanced contact tracing and spatial tracking of *Mycobacterium tuberculosis* infection by enumeration of antigen-specific T cells," *The Lancet* 357:2017-2021, Jun. 23, 2001.

Lalvani et al., "Enumeration of T Cells Specific for RD1-Encoded Antigens Suggests a High Prevalence of Latent *Mycobacterium tuberculosis* Infection in Healthy Urban Indians," *The Journal of Infectious Diseases* 183:469-477, 2001.

Lalvani et al., Rapid Detection of *Mycobacterium tuberculosis* Infection by Enumeration of Antigen-specific T Cells, *Am. J. Respir. Crit. Care Med.* 163:824-828, 2001.

(Continued)

*Primary Examiner* — Padmavathi Baskar
(74) *Attorney, Agent, or Firm* — Seed IP Law Group LLP

(57) ABSTRACT

The present invention refers to the use of gene sequences or portions thereof characterized in that the same belong to the classes of in vitro and ex vivo induced, repressed or conserved genes in *Mycobacterium tuberculosis* currently infected human macrophages and to corresponding peptides or consensus peptides or proteins for the preparation of specific bio-markers for the diagnosis and prevention of active or latent disease.

2 Claims, 8 Drawing Sheets

Figure 1:
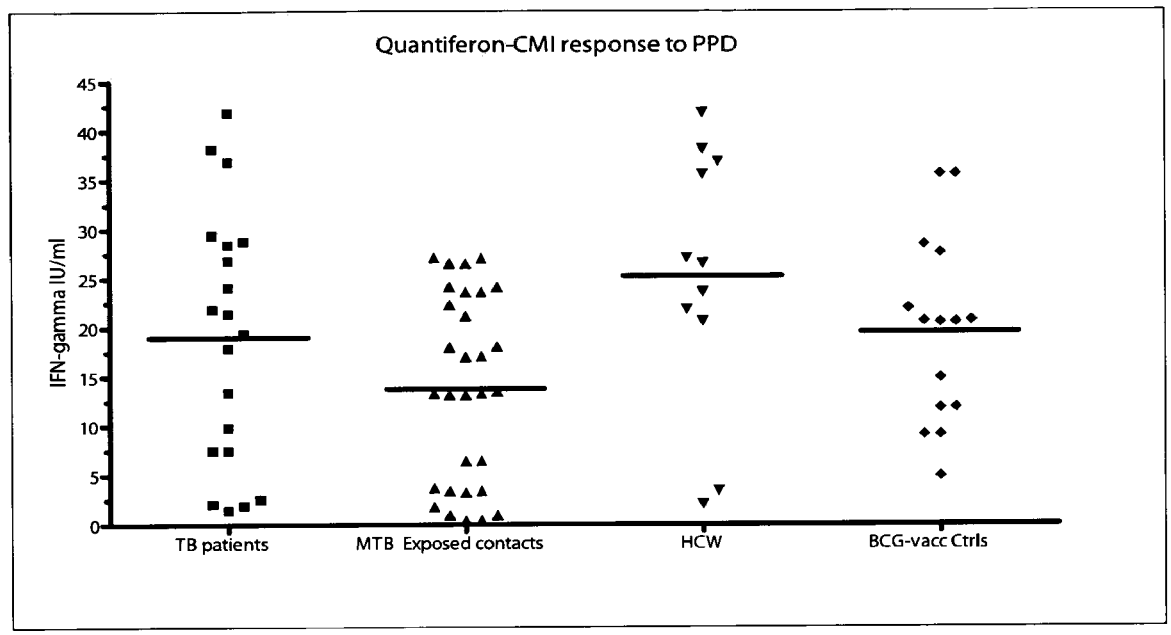

Specification includes a Sequence Listing.

(56) References Cited

OTHER PUBLICATIONS

Lawn et al., "Utility of interferon-γ ELISPOT assay responses in highly tuberculosis-exposed patients with advanced HIV infection in South Africa," *BMC Infectious Diseases 7*:99, Aug. 28, 2007, 9 pages.

Menzies et al., "Meta-analysis: New Tests for the Diagnosis of Latent Tuberculosis Infection: Areas of Uncertainty and Recommendations for Research," *Ann Intern Med. 146*:340-354, 2007.

Pai et al., "*Mycobacterium tuberculosis* Infection in Health Care Workers in Rural India: Comparison of a Whole-Blood Interferon γ Assay With Tuberculin Skin Testing," *JAMA 293*(22):2746-2755, Jun. 8, 2005.

Pathan et al., "Direct Ex Vivo Analysis of Antigen-Specific IFN-γ-Secreting CD4 T Cells in *Mycobacterium tuberculosis*-Infected Individuals: Associations with Clinical Disease State and Effect of Treatment, "*J Immunol 167*:5217-5225, 2001.

Ravn et al., "Human T Cell Responses to the ESAT-6 Antigen from *Mycobacterium tuberculosis*," *The Journal of Infectious Diseases 179*:637-645, 1999.

Seghrouchni et al. "Design of immunogenic peptides from *Mycobacterium tuberculosis* genes expressed during macrophage infection," *Tuberculosis 89*:210-217, 2009.

Shenoy et al., "New messages from old messengers: cAMP and *Mycobacteria*," *Trends in Microbiology 14*(12), 2006, 8 pages.

Ulrichs et al., "Differential T cell responses to *Mycobacterium tuberculosis* ESAT6 in tuberculosis patients and healthy donors," *Eur. J. Immunol. 28*:3949-3958, 1998.

Waters et al., "Use of Recombinant ESAT-6:CFP-10 Fusion Protein for Differentiation of Infections of Cattle by *Mycobacterium bovis* and by *M. avium* subsp. *avium* and *M. avium* subsp. *paratuberculosis*," *Clin. Diagn. Lab. Immunol. 11*(4): 729-735, 2004.

*Fig.11*

```
                        SEQUENCE LISTING

<160> NUMBER OF SEQ ID NOS: 87

<210> SEQ ID NO 1
<211> LENGTH: 20
<212> TYPE: PRT
<213> ORGANISM: Mycobacterium tuberculosis

<400> SEQUENCE: 1

Glu Met Trp Asp Ile Arg Asn Arg Gly Val Ile Pro Ala Gly Ala Leu
1               5                   10                  15

Pro Arg Val Arg
            20

<210> SEQ ID NO 2
<211> LENGTH: 30
<212> TYPE: PRT
<213> ORGANISM: Mycobacterium tuberculosis

<400> SEQUENCE: 2

Ala Lys Phe Arg Ser Val Arg Val Val Ile Thr Gly Ser Val Thr
1               5                   10                  15

Ala Ala Pro Val Arg Val Ser Glu Thr Leu Arg Arg Leu Ile
            20                  25                  30

<210> SEQ ID NO 3
<211> LENGTH: 13
<212> TYPE: PRT
<213> ORGANISM: Mycobacterium tuberculosis

<400> SEQUENCE: 3

Glu Ser Val Arg Leu Ala Phe Val Ala Ala Leu Gln His
1               5                   10

<210> SEQ ID NO 4
<211> LENGTH: 14
<212> TYPE: PRT
<213> ORGANISM: Mycobacterium tuberculosis

<400> SEQUENCE: 4

Gly Leu Leu Ile Thr Ile Arg Ser Pro Arg Ser Gly Ile Ala
1               5                   10
```

-continued

```
<210> SEQ ID NO 5
<211> LENGTH: 13
<212> TYPE: PRT
<213> ORGANISM: Mycobacterium tuberculosis

<400> SEQUENCE: 5

Ala Gln Leu Leu Trp Gln Leu Pro Leu Leu Ser Ile Gly
1               5                   10

<210> SEQ ID NO 6
<211> LENGTH: 27
<212> TYPE: PRT
<213> ORGANISM: Mycobacterium tuberculosis

<400> SEQUENCE: 6

Ala Asp Leu Val Arg Glu Leu Val Thr Ile Leu Pro Ile Val Leu Val
1               5                   10                  15

Ile Ala Ala Val Ala Ala Tyr Leu Leu Ser Arg
            20                  25

<210> SEQ ID NO 7
<211> LENGTH: 20
<212> TYPE: PRT
<213> ORGANISM: Mycobacterium tuberculosis

<400> SEQUENCE: 7

Ala Ala Tyr Leu Leu Ser Arg Ala Ala Leu Arg Pro Val Asp Arg Ile
1               5                   10                  15

Arg Ala Ala Ala
            20

<210> SEQ ID NO 8
<211> LENGTH: 20
<212> TYPE: PRT
<213> ORGANISM: Mycobacterium tuberculosis

<400> SEQUENCE: 8

Thr Thr Leu Asn Thr Met Leu Thr Arg Leu Gln Arg Ala Leu Ala His
1               5                   10                  15

Glu Gln Gln Phe
            20

<210> SEQ ID NO 9
<211> LENGTH: 21
<212> TYPE: PRT
<213> ORGANISM: Mycobacterium tuberculosis

<400> SEQUENCE: 9

Asp Leu Phe Val Ser Ile Asp Pro Asp His Leu Arg Arg Ile Leu Thr
1               5                   10                  15

Ala Val Leu Asp Asn
            20

<210> SEQ ID NO 10
<211> LENGTH: 17
<212> TYPE: PRT
<213> ORGANISM: Mycobacterium tuberculosis

<400> SEQUENCE: 10

Ser Gly Leu Gly Leu Ala Ile Val Ala Ala Leu Thr Thr Thr His Gly
1               5                   10                  15
```

Gly

<210> SEQ ID NO 11
<211> LENGTH: 19
<212> TYPE: PRT
<213> ORGANISM: Mycobacterium tuberculosis

<400> SEQUENCE: 11

Gly Arg Leu Pro Arg Lys Gly Pro Trp Gln Gln Lys Val Ile Lys Glu
1               5                   10                  15

Leu Pro Gln

<210> SEQ ID NO 12
<211> LENGTH: 20
<212> TYPE: PRT
<213> ORGANISM: Mycobacterium tuberculosis

<400> SEQUENCE: 12

Gly Lys Ile Val Val Leu Met Gly Ala Val Gly Thr Met Lys Pro Glu
1               5                   10                  15

Thr Gln Ala Ala
            20

<210> SEQ ID NO 13
<211> LENGTH: 14
<212> TYPE: PRT
<213> ORGANISM: Mycobacterium tuberculosis

<400> SEQUENCE: 13

Gly Glu Ile Ile Phe Ile Ser Gly Arg Leu Asn Gly Ala Ala
1               5                   10

<210> SEQ ID NO 14
<211> LENGTH: 13
<212> TYPE: PRT
<213> ORGANISM: Mycobacterium tuberculosis

<400> SEQUENCE: 14

Ala Arg Val Arg Ser Met Ser Pro Leu Glu Ile Ala Asp
1               5                   10

<210> SEQ ID NO 15
<211> LENGTH: 15
<212> TYPE: PRT
<213> ORGANISM: Mycobacterium tuberculosis

<400> SEQUENCE: 15

Glu Gln Ile Leu Phe Arg Arg Leu Ala Pro Phe Val Gly Gly Phe
1               5                   10                  15

<210> SEQ ID NO 16
<211> LENGTH: 14
<212> TYPE: PRT
<213> ORGANISM: Mycobacterium tuberculosis

<400> SEQUENCE: 16

Ala Ala Leu Val Arg Ala Leu Thr Ala Cys Gly Cys Ser Ser
1               5                   10

<210> SEQ ID NO 17
<211> LENGTH: 21
<212> TYPE: PRT
<213> ORGANISM: Mycobacterium tuberculosis -continued

```
<400> SEQUENCE: 17

Asp Lys Trp Thr Leu Cys Gln Ile Leu Tyr Trp Arg Gly Val Gly Thr
1               5                   10                  15

Cys Ile Ser Gly Asp
            20

<210> SEQ ID NO 18
<211> LENGTH: 17
<212> TYPE: PRT
<213> ORGANISM: Mycobacterium tuberculosis

<400> SEQUENCE: 18

Thr Lys Val Leu Gly Leu Tyr Thr Gln Ala Gln Val Leu Ala Tyr Cys
1               5                   10                  15

Gly

<210> SEQ ID NO 19
<211> LENGTH: 18
<212> TYPE: PRT
<213> ORGANISM: Mycobacterium tuberculosis

<400> SEQUENCE: 19

Asp Gln Val Thr Met His Gln Val Leu Met Ala Gln Leu Ala Leu Ala
1               5                   10                  15

Gly Gly

<210> SEQ ID NO 20
<211> LENGTH: 22
<212> TYPE: PRT
<213> ORGANISM: Mycobacterium tuberculosis

<400> SEQUENCE: 20

Glu Gly Val Arg Leu Leu Gly Ala Ala Ala Ala Leu Arg Gln Gln Thr
1               5                   10                  15

Arg Gln Val Arg Phe Lys
            20

<210> SEQ ID NO 21
<211> LENGTH: 13
<212> TYPE: PRT
<213> ORGANISM: Mycobacterium tuberculosis

<400> SEQUENCE: 21

Glu Leu Met Ala Arg Ala Ala Val Leu Gly Ser Ala His
1               5                   10

<210> SEQ ID NO 22
<211> LENGTH: 13
<212> TYPE: PRT
<213> ORGANISM: Mycobacterium tuberculosis

<400> SEQUENCE: 22

Ala Val Ile Val Arg Ser Glu Leu Leu Thr Gln Tyr Leu
1               5                   10

<210> SEQ ID NO 23
<211> LENGTH: 20
<212> TYPE: PRT
<213> ORGANISM: Mycobacterium tuberculosis

<400> SEQUENCE: 23

Gly Thr Leu Arg His Leu Asp Pro Pro Val Arg Arg Ser Gly Gly Arg
```

```
1               5                  10                 15
Glu Gln His Leu
        20

<210> SEQ ID NO 24
<211> LENGTH: 13
<212> TYPE: PRT
<213> ORGANISM: Mycobacterium tuberculosis

<400> SEQUENCE: 24

Thr Ala Trp Ile Thr Ala Val Val Pro Gly Leu Met Val
1               5                   10

<210> SEQ ID NO 25
<211> LENGTH: 13
<212> TYPE: PRT
<213> ORGANISM: Mycobacterium tuberculosis

<400> SEQUENCE: 25

Ala Pro Met Val Phe Ser Ala Thr Lys Gly Met Thr Ala
1               5                   10

<210> SEQ ID NO 26
<211> LENGTH: 14
<212> TYPE: PRT
<213> ORGANISM: Mycobacterium tuberculosis

<400> SEQUENCE: 26

Thr Cys Ala Met Arg Arg Leu Ala His Arg Phe Ser Gly Gly
1               5                   10

<210> SEQ ID NO 27
<211> LENGTH: 13
<212> TYPE: PRT
<213> ORGANISM: Mycobacterium tuberculosis

<400> SEQUENCE: 27

Ser Val Val Arg Arg Lys Gln Thr Leu Leu Ser Ala Gln
1               5                   10

<210> SEQ ID NO 28
<211> LENGTH: 13
<212> TYPE: PRT
<213> ORGANISM: Mycobacterium tuberculosis

<400> SEQUENCE: 28

Gly Val Val His Arg Asn Pro Ala Val Thr Val Ala Glu
1               5                   10

<210> SEQ ID NO 29
<211> LENGTH: 22
<212> TYPE: PRT
<213> ORGANISM: Mycobacterium tuberculosis

<400> SEQUENCE: 29

Pro Gly Val Val Ala Thr His Ala Val Arg Thr Leu Gly Thr Thr Gly
1               5                   10                  15

Ser Arg Ala Ile Gly Leu
            20

<210> SEQ ID NO 30
<211> LENGTH: 25
<212> TYPE: PRT
<213> ORGANISM: Mycobacterium tuberculosis
```

<400> SEQUENCE: 30

Pro Gln Trp Arg Arg Ala Arg Val Arg Leu Cys Gly Arg Trp Trp Arg
1               5                   10                  15

Arg Ser Asn Thr Thr Arg Gly Ala Ser
            20                  25

<210> SEQ ID NO 31
<211> LENGTH: 18
<212> TYPE: PRT
<213> ORGANISM: Mycobacterium tuberculosis

<400> SEQUENCE: 31

Ala Arg Leu Met Val Gly Ala Val Arg Arg His Arg Pro Gly Ser Leu
1               5                   10                  15

Gln Arg

<210> SEQ ID NO 32
<211> LENGTH: 12
<212> TYPE: PRT
<213> ORGANISM: Mycobacterium tuberculosis

<400> SEQUENCE: 32

Ala Ala Met Arg Asn Met Lys Ser Thr Ser His Glu
1               5                   10

<210> SEQ ID NO 33
<211> LENGTH: 14
<212> TYPE: PRT
<213> ORGANISM: Mycobacterium tuberculosis

<400> SEQUENCE: 33

Gln Thr Ile Val Met Leu Trp Thr Ala Ala Val Gly Cys Ala
1               5                   10

<210> SEQ ID NO 34
<211> LENGTH: 19
<212> TYPE: PRT
<213> ORGANISM: Mycobacterium tuberculosis

<400> SEQUENCE: 34

Leu Cys Met Leu Met Leu Gly Leu Leu Met Leu Ile Phe Ser Glu His
1               5                   10                  15

Arg Ser Ser

<210> SEQ ID NO 35
<211> LENGTH: 20
<212> TYPE: PRT
<213> ORGANISM: Mycobacterium tuberculosis

<400> SEQUENCE: 35

Ser Ala Leu Val Leu Val Gly Leu Gly Leu Cys Gly Ser Gly Val Ala
1               5                   10                  15

Leu Cys Leu Thr
            20

<210> SEQ ID NO 36
<211> LENGTH: 16
<212> TYPE: PRT
<213> ORGANISM: Mycobacterium tuberculosis

<400> SEQUENCE: 36

```
Ser Glu Leu Val Arg Phe Glu Leu Leu Ala Gly Val Arg Glu Ser Glu
1               5                   10                  15
```

<210> SEQ ID NO 37
<211> LENGTH: 14
<212> TYPE: PRT
<213> ORGANISM: Mycobacterium tuberculosis

<400> SEQUENCE: 37

```
Val Asp Tyr Leu Ile Ala Ala Thr Ala Ile Val Val Asp Ala
1               5                   10
```

<210> SEQ ID NO 38
<211> LENGTH: 15
<212> TYPE: PRT
<213> ORGANISM: Mycobacterium tuberculosis

<400> SEQUENCE: 38

```
Gln Gly Ile Glu Tyr Tyr Lys Ser Ser Val Leu Pro Gln Ile Glu
1               5                   10                  15
```

<210> SEQ ID NO 39
<211> LENGTH: 16
<212> TYPE: PRT
<213> ORGANISM: Mycobacterium tuberculosis

<400> SEQUENCE: 39

```
Glu Gly Trp Ile Val Tyr Ala Arg Ser Thr Thr Ile Gln Ala Gln Ser
1               5                   10                  15
```

<210> SEQ ID NO 40
<211> LENGTH: 10
<212> TYPE: PRT
<213> ORGANISM: Mycobacterium tuberculosis

<400> SEQUENCE: 40

```
Thr Arg Arg Met Tyr Ser Asn Tyr Gly Phe
1               5                   10
```

<210> SEQ ID NO 41
<211> LENGTH: 23
<212> TYPE: PRT
<213> ORGANISM: Mycobacterium tuberculosis

<400> SEQUENCE: 41

```
Phe Gly Tyr Arg Val Gln Glu Ser Ala Phe Glu Ala Met Leu Thr Lys
1               5                   10                  15

Gly Gln Leu Ala Lys Leu Val
            20
```

<210> SEQ ID NO 42
<211> LENGTH: 26
<212> TYPE: PRT
<213> ORGANISM: Mycobacterium tuberculosis

<400> SEQUENCE: 42

```
Asp Asn Ile Arg Ile Tyr Lys Ile Arg Gly Val Ala Ala Val Thr Phe
1               5                   10                  15

Tyr Gly Arg Gly Arg Leu Val Ser Ala Glu
            20                  25
```

<210> SEQ ID NO 43
<211> LENGTH: 23
<212> TYPE: PRT

-continued

<213> ORGANISM: Mycobacterium tuberculosis

<400> SEQUENCE: 43

Arg Ser Tyr Ile Leu Arg Ala Gly Ile Ser Ser Leu Phe Arg Tyr Ile
1 5 10 15

Glu Gly Val His Gly Glu Arg
20

<210> SEQ ID NO 44
<211> LENGTH: 20
<212> TYPE: PRT
<213> ORGANISM: Mycobacterium tuberculosis

<400> SEQUENCE: 44

Ser Ala Met Arg Pro Gln Asp Arg Leu Leu Val Gly Asn Trp Val Asp
1 5 10 15

Asp Ser Leu Leu
20

<210> SEQ ID NO 45
<211> LENGTH: 13
<212> TYPE: PRT
<213> ORGANISM: Mycobacterium tuberculosis

<400> SEQUENCE: 45

Leu Tyr Leu Val Gly Leu Glu Pro Tyr Val Gln Phe Glu
1 5 10

<210> SEQ ID NO 46
<211> LENGTH: 13
<212> TYPE: PRT
<213> ORGANISM: Mycobacterium tuberculosis

<400> SEQUENCE: 46

Ala Gly Phe Arg Ile Leu Glu Ala Arg Arg Phe Pro Ile
1 5 10

<210> SEQ ID NO 47
<211> LENGTH: 19
<212> TYPE: PRT
<213> ORGANISM: Mycobacterium tuberculosis

<400> SEQUENCE: 47

Ile Arg Tyr Arg Ala Arg Tyr Val Asn Gly Gln Leu Asn Met Cys Leu
1 5 10 15

Ala Arg Ile

<210> SEQ ID NO 48
<211> LENGTH: 16
<212> TYPE: PRT
<213> ORGANISM: Mycobacterium tuberculosis

<400> SEQUENCE: 48

Ala Leu Leu Val Ala Tyr Leu Pro Ala Arg Ser Arg Glu Glu Met Phe
1 5 10 15

<210> SEQ ID NO 49
<211> LENGTH: 13
<212> TYPE: PRT
<213> ORGANISM: Mycobacterium tuberculosis

<400> SEQUENCE: 49

Asn Arg Leu Arg Leu Ala Ala Thr His Ala Val Arg Thr

<210> SEQ ID NO 50
<211> LENGTH: 21
<212> TYPE: PRT
<213> ORGANISM: Mycobacterium tuberculosis

<400> SEQUENCE: 50

Ala Pro Leu Gln Arg Arg Phe Arg Asp Ala Phe Thr Ala Thr Ala His
1               5                   10                  15

Phe Gln Val Asn Glu
            20

<210> SEQ ID NO 51
<211> LENGTH: 18
<212> TYPE: PRT
<213> ORGANISM: Mycobacterium tuberculosis

<400> SEQUENCE: 51

Ser Arg Glu Leu Pro Gly Arg Val Leu Leu Asp Gln Pro Ala Asp Val
1               5                   10                  15

Ser Met

<210> SEQ ID NO 52
<211> LENGTH: 18
<212> TYPE: PRT
<213> ORGANISM: Mycobacterium tuberculosis

<400> SEQUENCE: 52

Glu Pro Val Val Thr Val Asp Val Thr Ala Met Ser Ala Val Leu Glu
1               5                   10                  15

Ile Asp

<210> SEQ ID NO 53
<211> LENGTH: 23
<212> TYPE: PRT
<213> ORGANISM: Mycobacterium tuberculosis

<400> SEQUENCE: 53

Ala Val Ile Gln Val Ser Asp Arg Ala Val Arg Gly Trp Arg Thr Gly
1               5                   10                  15

Asp Ile Arg Pro Glu Arg Tyr
            20

<210> SEQ ID NO 54
<211> LENGTH: 17
<212> TYPE: PRT
<213> ORGANISM: Mycobacterium tuberculosis

<400> SEQUENCE: 54

Pro Asp Leu Arg Gly Ala Leu Leu Ala Val Thr Leu Gly Leu Val
1               5                   10                  15

Thr

<210> SEQ ID NO 55
<211> LENGTH: 16
<212> TYPE: PRT
<213> ORGANISM: Mycobacterium tuberculosis

<400> SEQUENCE: 55

Pro Asp Trp Gly Trp Leu Ser Val Ala Thr Val Gly Ser Phe Leu Ala
1               5                   10                  15

```
<210> SEQ ID NO 56
<211> LENGTH: 21
<212> TYPE: PRT
<213> ORGANISM: Mycobacterium tuberculosis

<400> SEQUENCE: 56

Gly Ala Val Leu Gly Val Ala Val Met Val Ile Leu Ile Gly Lys Pro
1               5                   10                  15

Glu His Gly Thr Ala
            20

<210> SEQ ID NO 57
<211> LENGTH: 15
<212> TYPE: PRT
<213> ORGANISM: Mycobacterium tuberculosis

<400> SEQUENCE: 57

Ala Ala Ile Cys Phe Ile Ala Val Ala Val Ala Ala Val Leu
1               5                   10                  15

<210> SEQ ID NO 58
<211> LENGTH: 15
<212> TYPE: PRT
<213> ORGANISM: Mycobacterium tuberculosis

<400> SEQUENCE: 58

Thr Lys Leu Val Arg Leu Thr Lys Ala Gln Phe Asp Glu Ile Ala
1               5                   10                  15

<210> SEQ ID NO 59
<211> LENGTH: 14
<212> TYPE: PRT
<213> ORGANISM: Mycobacterium tuberculosis

<400> SEQUENCE: 59

Ala Asp Leu Val Leu Ala Gly Pro Ala Ala Ser Arg Glu His
1               5                   10

<210> SEQ ID NO 60
<211> LENGTH: 16
<212> TYPE: PRT
<213> ORGANISM: Mycobacterium tuberculosis

<400> SEQUENCE: 60

Tyr Ala Tyr Glu Tyr Phe Ile Arg His Asn Pro Leu Ser Asp Tyr Ala
1               5                   10                  15

<210> SEQ ID NO 61
<211> LENGTH: 18
<212> TYPE: PRT
<213> ORGANISM: Mycobacterium tuberculosis

<400> SEQUENCE: 61

Phe Pro Val Arg Gly Leu Val Arg Gly Arg Arg Thr Leu Thr Leu Leu
1               5                   10                  15

Glu Ala

<210> SEQ ID NO 62
<211> LENGTH: 16
<212> TYPE: PRT
<213> ORGANISM: Mycobacterium tuberculosis

<400> SEQUENCE: 62
```

```
Glu Val Leu Arg Ile Leu Arg Arg Ser Leu Ala Ala Leu Arg Ala
1               5                   10                  15
```

<210> SEQ ID NO 63
<211> LENGTH: 18
<212> TYPE: PRT
<213> ORGANISM: Mycobacterium tuberculosis

<400> SEQUENCE: 63

```
Arg Val Ile Leu His Ser Pro Tyr Gly Leu Arg Val His Gly Pro Leu
1               5                   10                  15

Ala Leu
```

<210> SEQ ID NO 64
<211> LENGTH: 15
<212> TYPE: PRT
<213> ORGANISM: Mycobacterium tuberculosis

<400> SEQUENCE: 64

```
Ala Ala Trp Val Ile Asn Gly Leu Ala Asn Ala Tyr Asn Asp Thr
1               5                   10                  15
```

<210> SEQ ID NO 65
<211> LENGTH: 27
<212> TYPE: PRT
<213> ORGANISM: Mycobacterium tuberculosis

<400> SEQUENCE: 65

```
Asp Gln Tyr Arg Ala Arg Asn Val Ala Val Met Asn Ala Tyr Val Ser
1               5                   10                  15

Trp Thr Arg Ser Ala Leu Ser Asp Leu Pro Arg
            20                  25
```

<210> SEQ ID NO 66
<211> LENGTH: 25
<212> TYPE: PRT
<213> ORGANISM: Mycobacterium tuberculosis

<400> SEQUENCE: 66

```
Ser Asp Leu Leu Ala Asp Ala Val Glu Arg Tyr Leu Gln Trp Leu Ser
1               5                   10                  15

Lys Ser Ser Ser Gln Leu Lys His Ala
            20                  25
```

<210> SEQ ID NO 67
<211> LENGTH: 13
<212> TYPE: PRT
<213> ORGANISM: Mycobacterium tuberculosis

<400> SEQUENCE: 67

```
Gly Pro Val Val Val His Pro Ser Trp Trp Ser Ala Ala
1               5                   10
```

<210> SEQ ID NO 68
<211> LENGTH: 16
<212> TYPE: PRT
<213> ORGANISM: Mycobacterium tuberculosis

<400> SEQUENCE: 68

```
Ile Thr Ala Val Val Leu Ile Asp Val Pro Ser Thr Val Ala Gly Ala
1               5                   10                  15
```

-continued

<210> SEQ ID NO 69
<211> LENGTH: 14
<212> TYPE: PRT
<213> ORGANISM: Mycobacterium tuberculosis

<400> SEQUENCE: 69

Ala Ala Val Val Arg His Gly Ala Thr Thr Leu Gln Arg Pro
1               5                   10

<210> SEQ ID NO 70
<211> LENGTH: 18
<212> TYPE: PRT
<213> ORGANISM: Mycobacterium tuberculosis

<400> SEQUENCE: 70

Arg Pro Val Arg Arg Val Leu Leu Phe Val Val Pro Ser Ser Gly Pro
1               5                   10                  15

Ala Pro

<210> SEQ ID NO 71
<211> LENGTH: 24
<212> TYPE: PRT
<213> ORGANISM: Mycobacterium tuberculosis

<400> SEQUENCE: 71

Gly Ser Val Arg Gln Leu Pro Ser Val Leu Lys Pro Pro Leu Ile Thr
1               5                   10                  15

Leu Arg Thr Leu Thr Leu Ser Gly
            20

<210> SEQ ID NO 72
<211> LENGTH: 18
<212> TYPE: PRT
<213> ORGANISM: Mycobacterium tuberculosis

<400> SEQUENCE: 72

Gly Ala Val Leu Arg Leu Val Val Arg Phe Ala Glu Pro Leu Pro Pro
1               5                   10                  15

Ser Pro

<210> SEQ ID NO 73
<211> LENGTH: 19
<212> TYPE: PRT
<213> ORGANISM: Mycobacterium tuberculosis

<400> SEQUENCE: 73

Ala Gly Tyr Leu Leu Thr Tyr Thr Ile Ala Asn Asn Gly Lys Glu Phe
1               5                   10                  15

Ala Glu Leu

<210> SEQ ID NO 74
<211> LENGTH: 18
<212> TYPE: PRT
<213> ORGANISM: Mycobacterium tuberculosis

<400> SEQUENCE: 74

Ala Ala Val Arg Lys Arg Met Val Ile Gly Leu Ser Thr Gly Ser Asp
1               5                   10                  15

Asp Asp

<210> SEQ ID NO 75
<211> LENGTH: 20

-continued

```
<212> TYPE: PRT
<213> ORGANISM: Mycobacterium tuberculosis

<400> SEQUENCE: 75

Ala Leu Leu Leu Arg Asp Val Leu Gln Trp Lys Ser Ala Glu Val Ala
1               5                   10                  15

Asp Ala Ile Gly
            20

<210> SEQ ID NO 76
<211> LENGTH: 25
<212> TYPE: PRT
<213> ORGANISM: Mycobacterium tuberculosis

<400> SEQUENCE: 76

Asn Ser Leu Leu Gln Arg Ala Arg Ser Gln Leu Gln Thr Val Arg Pro
1               5                   10                  15

Ser Ala Ala Asp Arg Leu Ser Ala Ala
            20                  25

<210> SEQ ID NO 77
<211> LENGTH: 20
<212> TYPE: PRT
<213> ORGANISM: Mycobacterium tuberculosis

<400> SEQUENCE: 77

Met Ser Trp Val Met Val Ser Pro Glu Leu Val Val Ala Ala Ala Ala
1               5                   10                  15

Asp Leu Ala Gly
            20

<210> SEQ ID NO 78
<211> LENGTH: 17
<212> TYPE: PRT
<213> ORGANISM: Mycobacterium tuberculosis

<400> SEQUENCE: 78

Ala Ala Phe Tyr Ala Gln Phe Val Gln Ala Leu Thr Ser Gly Gly Ala
1               5                   10                  15

Tyr

<210> SEQ ID NO 79
<211> LENGTH: 14
<212> TYPE: PRT
<213> ORGANISM: Mycobacterium tuberculosis

<400> SEQUENCE: 79

Ala Leu Leu Val Arg Met Pro Thr Ser Leu Pro Ala Val Ala
1               5                   10

<210> SEQ ID NO 80
<211> LENGTH: 27
<212> TYPE: PRT
<213> ORGANISM: Mycobacterium tuberculosis

<400> SEQUENCE: 80

Ser Arg Leu Arg Thr His Val Arg Pro Asp Ala Pro Leu Val Pro Leu
1               5                   10                  15

Ala Leu Arg Val Asp Gly Leu Arg Ser Arg Trp
            20                  25

<210> SEQ ID NO 81
```

```
<211> LENGTH: 14
<212> TYPE: PRT
<213> ORGANISM: Mycobacterium tuberculosis

<400> SEQUENCE: 81

Ala Ala Val Leu Thr Met Leu Gly Val Ala Gly Tyr Gly Trp
1               5                   10

<210> SEQ ID NO 82
<211> LENGTH: 21
<212> TYPE: PRT
<213> ORGANISM: Mycobacterium tuberculosis

<400> SEQUENCE: 82

Gly Leu Phe Met Ile Phe Leu Asp Ala Leu Ile Val Asn Val Ala Leu
1               5                   10                  15

Pro Asp Ile Gln Arg
            20

<210> SEQ ID NO 83
<211> LENGTH: 25
<212> TYPE: PRT
<213> ORGANISM: Mycobacterium tuberculosis

<400> SEQUENCE: 83

Ser Trp Val Val Ala Ser Tyr Ser Leu Gly Met Ala Val Phe Ile Met
1               5                   10                  15

Ser Ala Gly Thr Leu Ala Asp Leu Leu
            20                  25

<210> SEQ ID NO 84
<211> LENGTH: 25
<212> TYPE: PRT
<213> ORGANISM: Mycobacterium tuberculosis

<400> SEQUENCE: 84

Gln Gln Trp Asn Phe Ala Gly Ile Glu Ala Ala Ala Ser Ala Ile Gln
1               5                   10                  15

Gly Asn Val Thr Ser Ile His Ser Leu
            20                  25

<210> SEQ ID NO 85
<211> LENGTH: 13
<212> TYPE: PRT
<213> ORGANISM: Mycobacterium tuberculosis

<400> SEQUENCE: 85

Leu Ala Trp Ile Thr Ala Val Val Pro Gly Leu Met Val
1               5                   10

<210> SEQ ID NO 86
<211> LENGTH: 12
<212> TYPE: PRT
<213> ORGANISM: Mycobacterium tuberculosis

<400> SEQUENCE: 86

Gly Glu Ile Ile Phe Ile Ser Gly Arg Leu Asn Gly
1               5                   10

<210> SEQ ID NO 87
<211> LENGTH: 14
<212> TYPE: PRT
<213> ORGANISM: Mycobacterium tuberculosis
```

```
<400> SEQUENCE: 87

Ser Ala Leu Leu Arg Arg Leu Ser Thr Cys Pro Pro Glu Ser
1               5                   10
```

USE OF AMINO ACID SEQUENCES FROM *MYCOBACTERIUM TUBERCULOSIS* OR CORRESPONDING NUCLEIC ACIDS FOR DIAGNOSIS AND PREVENTION OF TUBERCULAR INFECTION, DIAGNOSTIC KIT AND VACCINE THEREFROM

STATEMENT REGARDING SEQUENCE LISTING

The Sequence Listing associated with this application is provided in text format in lieu of a paper copy, and is hereby incorporated by reference into the specification. The name of the text file containing the Sequence Listing is 830109_424_D4_SEQUENCE_LISTING.txt. The text file is 20.9 KB, was created on Aug. 14, 2020, and is being submitted electronically via EFS-Web.

The present invention concerns the use of amino acid sequences from *Mycobacterium tuberculosis* or corresponding nucleic acids thereof for diagnosis and prevention of tubercular infection, diagnostic kit and vaccine therefrom.

More particularly the invention refers to the use of gene sequences or portions thereof characterized in that the same belong to the classes of in vitro and ex vivo induced, repressed or conserved genes in *Mycobacterium tuberculosis* currently infected human macrophages and corresponding peptides or consensus peptides or proteins for the preparation of specific bio-markers for diagnosis and prevention of active or latent disease.

The laboratory diagnosis of tubercular infection and active disease onset is a very important in order to guarantee specificity, rapidity and effectiveness of the therapeutic treatment.

As to the active tubercular disease, current diagnostic protocols are based on microscopic, culture or molecular methods. With reference to microscopic examination, high mycobacteria concentrations in biological sample (from 5 to 10000/ml) are needed in order a positive result to be obtained and the sensitivity is generally lower than 60% with reduced specificity due to the inability of the test to discriminate MTB and not tubercular mycobacteria.

As to culture tests, the use thereof does not assure the medical report to be carried out within acceptable time period. In fact, MTB colonies are visible only 10-24 days after the seed thereof in solid or liquid culture media (1), as the bacterium grows slowly in vitro. Furthermore culture tests, although considered highly sensitive, produce about 10-30% rate of negative false results and are expensive.

Molecular biology tests are highly sensitive and specific, with a sensitivity comparable to culture tests and the ability of quickly discrimination of MTB and not tubercular mycobacteria. However, the sensitivity thereof is meaningfully lower for samples containing low mycobacteria concentration, that is those negatives to microscopic examination, moreover only highly specialized laboratories can use the same being thus very expensive.

Tuberculosis is still a world-wide public health emergency lacking necessary economic resources in order an efficient diagnosis and treatment program to be planned in high incidence countries and being hardly diagnosable in affected population segments in low incidence industrialized countries.

Currently, in high incidence countries, TB active diagnosis is based on MTB microscopic (40-90% sensitivity) and culture (70-90% sensitivity) examination with 2-6 week waiting times for culture tests. In low incidence industrialized countries, TB active diagnosis is based on microscopic and culture tests and, for not tubercular MTB and mycobacteria discrimination or microscopically negative samples, on molecular tests (70-90% sensitivity).

As to the diagnosis of latent or not active tubercular infection, traditional diagnostic test is tuberculin skin test, an in vivo economic and quick diagnostic test that, standardized in years '50 allows the possibility the infection to be detected carefully and quickly thus allowing essential epidemiological surveys about tubercular infection incidence and prevalence to be carried out. Tuberculin test from the point of view of public health allowed infection incidence and prevalence to be monitored in order a global disease control to be obtained and, from the point of view of preventive and clinical medicine, infected contacts by active TB bearers to be identified allowing to establish therapeutic protections against tubercular infection aiming to prevent new case onsets. Therefore latent infection diagnosis is a fundamental element of the fight against the tuberculosis both in high and low incidence countries Various cellular and molecular immunological issues demonstrated that the contact with MTB or antigens thereof in vitro elicits a strong cell-mediated response characterized by high production of interferon-γ (IFN-γ). This suggested that the identification of IFN-γ releasing T-lymphocytes or measure of cytokine itself, as response to the *Mycobacterium* or antigen thereof, represents a way in order already occurred infection to be diagnosed equivalently to tuberculin test.

With respect to this issue recently two kits for tubercular infection diagnosis, i.e. QuantiFERON-TB Gold and T-SPOT TB, have been commercialized, said kits using proteins or peptides based on MTB genes, belonging to MTB genome RD1 differentiation region, in order to stimulate the IFN-γ production in T lymphocytes of circulating blood. The cost of kits is quite high in order to be used on wide scale in tuberculosis high incidence countries. The sensitivity of two commercial kits is similar, being sensitivity and specificity range from 70 to 90% and from 80 to 95%, respectively. (2). Moreover, sensitivity and specificity of these kits used in Tuberculosis high incidence areas as compared to traditionally used tuberculin test are still debated. In fact there are cases wherein the skin test proves to be even more sensitive than Quantiferon (3) and cases wherein the two tests are exactly comparable (4).

Major limits of still more widely used tuberculin skin test, carried out according to multi puncture method or Mantoux intradermal injection, are operating complexity and insufficient specificity. In fact, the test involves a first and a second patient visit for tuberculin injection and test reading by specialized sanitary staff, respectively. For the staff the contamination risk by intradermal injection syringes in case of TB-HIV co-infection occurs. As to the tuberculin test specificities, it is known that purified tuberculin protein derivative (Purified protein derivative, PPD) displays cross-reactivity with *M. bovis* Bacillus Calmette-Guerin (BCG) used for antitubercular vaccination and various environmental not tubercular mycobacteria, displaying high sequence homology with Kock bacillus genome (5, 6). Therefore, BCG vaccinated or also subjects recently in contact with MTB virulent species, i.e. as in research laboratories named, collection strain H37Rv (ATCC 27294), will be tuberculin test positive, even if with lower reaction intensity than MTB infected subjects. For this reason, positivity intensity limits discriminating MTB reactivity from that resulting from anti *M. bovis* BCG or non tubercular mycobacteria immunity, have been established.

Such intensity limits, however, are not sufficiently specific in order the tubercular infection in a vaccinated or environmental mycobacteria extensively exposed population to be diagnosed.

With respect to prevention of MTB infection the unique currently available vaccine for tubercular disease prophylaxis is *M. bovis* Bacillus Calmette-Guerin (BCG) (ATCC 27291), a vaccine based on an avirulent *M. bovis* strain, used all over the world from approximately 75 years.

In the light of above therefore it is apparent the need to provide for new diagnostic kits and vaccines based on specific peptide use suitable to overcome the disadvantages of up to now known art.

There are several studies correlating peripheral blood lymphocyte response to MTB proteins and peptides in the presence of latent infection, or recent contact with TB patients, and tubercular active disease using ELISPOT analysis for the detection of blood mononucleated cells suitable to produce IFN-γ as a result of stimulation (7-15). ELISPOT is a technique allowing, by stimulation of mononucleated blood cells on culture plate using sensitizing antibodies directed against cytokine (for example IFN-γ), the frequency of cytokine producing T lymphocytes as a response to stimulation with one or more antigens, which can be proteins, peptides or other target molecules, to be detected.

T lymphocytes recognize the antigen using the antigen T cell receptor (TCR) when the antigen is presented in peptide form (8-12 amino acid long), representing the epitope, bound to a molecule of histocompatibility major complex (MHC), a receptor family expressed on the plasmatic membrane of all the nucleated cells (as to class I MHC molecules) and antigen presenting cells like dendritic cells, macrophages etc. (as to class II MHC molecules). In humans MHC system is represented by various isotype variants, HLA-A, HLA-B and HLA-C for class I molecules; HLA-DP, HLA-DQ and HLA-DR for class II molecules. Each of said molecules displays a different number of allelic variants. Since T cell TCR recognized antigen repertoire is related to the ability of subject antigen presenting cell MHC receptors to bind peptides derived from the digestion of antigenic proteins, the indispensable condition in order the peptide to be recognised as antigen and therefore suitable to activate antigenic protein specific T lymphocytes is the susceptibility thereof to be bound by MHC receptors.

Genes encoding for HLA molecules are among most polymorphic genes occurring in human genome. It is noteworthy in this context the fact that many differences among individual allelic products of these molecules are variations of bases encoding for amino acid sequence modifications of regions involved in antigenic peptide binding. These sequence variations determine the binding properties of different allelic variants of HLA molecules and therefore the antigenic peptide repertoire with which said allelic variant will be able to form a tri-molecular complex together with T lymphocytes TCR and activate said lymphocytes.

In the context of MTB protein antigen recognizing, it is to be pointed out that every single mycobacterial epitope can be bound to one or more HLA allelic variants, but not necessarily all allelic variants expressed in a population. Moreover, since each not homozygote subject expresses at least two allelic variants of HLA-A, HLA-B, HLA-C, HLA-DP, HLA-DQ and two to four HLA-DR variants, in various subjects comprising the population under investigation different epitopes can be recognized in the context of the same or different allelic variants of different isotypes.

It is therefore apparent that the peptide set suitable to bind various allelic variants of HLA isotypes expressed by every single subject in a population can be different. From above it results the need to use an antigenic peptide set suitable to represent in as exhaustive as possible way MTB peptide epitope repertoire recognized by T lymphocytes from subjects of the population under investigation. In this context it is to be pointed out that, although the whole MTB genome has been sequenced and is available to be studied, the antigens up to now used in immunological tests for tubercular infection diagnosis result from research about *Mycobacterium* biochemical characterization during the in vitro growth step thereof in culture media and not from ex vivo experiments.

Patent application US2006/0115847 discloses an immunological diagnostic method for *M. tuberculosis* infection based on the combination of epitopes from proteins encoded by *M. tuberculosis* genome regions not occurring in BCG vaccine or most common not tubercular mycobacteria. The experimental part of said patent application reports results about various tested proteins, however the distribution of patient responses to single peptides is quite not homogeneous, in fact, as FIG. 1 shows, several TB patients are peptide insensitive. As to the patient response frequency to selected peptides, in table 6 it is shown that best individually tested peptide CFP10 induces a response in 10/15 patients, i.e. a 66.66% response frequency. Further, by means of combination of some peptides, as shown in table 7 of the US patent, sensitivity results of 92% for latent TB, i.e. PPD+ patients, 88% for active TB and 90% for TB patients under antibiotic treatment, have been obtained.

In prior studies, the authors of the present invention have identified a group of genes preferentially transcribed by human macrophages infecting MTB and characterized in that said genes belong to deletion regions of *M. bovis*-BCG vaccine species (WO 2005/021790).

The authors of the present invention now have analyzed proteins expressed by MTB in human macrophages, both in in vitro primary cultures, and or ex vivo in bronchoalveolar lavage (BAL) samples from active pulmonary TB patients. Using a software developed by the applicants allowing the ability of class II histocompatibility molecules to bind peptides of whole MTB genome to be analysed, some proteins, proved to be remarkably effective from the immunological point of view, have been selected. In summary, the study compared *M. tuberculosis* gene expression in three different growth environments: synthetic medium culture (Sauton's), monocyte-derived-human macrophage (MDM) infected in vitro with *M. tuberculosis*, alveolar macrophage (AM) from bronchoalveolar lavage (BAL) samples of pulmonary TB affected patients before the antibiotic therapy.

From thus obtained 9 gene groups, first 100 proteins, according to a combination criteria (modulation of expression, immunogenicity, tubercular Complex specificity, etc), have been selected. From these 100 proteins again a 30 protein group has been selected, for which a positive response in immunological tests on TB patients whole blood had been obtained (see table 1).

After an ulterior selection from 4 groups of subjects: Pulmonary TB before antibiotic therapy (n=13), recently exposed healthy contacts (TB patient relatives) PPD+ (n=8); long term TB patient exposed healthy contacts (professional exposure of hospital workers) PPD+ (n=5); BCG vaccinated negative controls, PPD− (n=4), firstly 43 peptides have been designed, synthesized and tested.

Then the 6 most sensible and specific peptides have been selected (see table 2), and the study has been repeated using an extended subject sample (see tables 3-5 and FIGS. 1-7).

The results obtained using said six peptides and a peptide belonging to ESAT6, i.e an highly immunogenic protein occurring in both above mentioned commercial kits (FIG. 8), have been compared.

In summary, all the selected peptides displayed T-cell reactivity. Particularly, peptide #3 (SEQ ID NO:71 of the present invention) displays an elevated sensitivity comparable, if not more elevated, to multiepitope ESAT-6 protein derived control peptide. It is noteworthy that, as in panel estimated (i.e. by estimating ex-post total data of each individual peptide), 6 multiepitope peptides are recognized by about 75% of the subjects with active TB (a result comparable, in this series, to Quantiferon-TB gold in-Tube, as shown in Table 4). Data are perfectly similar to the result obtained in a patient subgroup tested using said 6 peptides concurrently in the same well (as shown in Table 5).

Peptide optimal diagnostic sensitivity is associated together with an optimal specificity. In fact, the reported peptide response is limited to active TB subjects, recent exposure contacts and exposed sanitary staff (as shown in Table 4 and FIG. 9). It is noteworthy that, although the data must be supported by larger subject number, no peptide response from *M. bovis* BCG antitubercular vaccinated control subjects, not even from Quantiferon-TB gold in-Tube positive 3 subjects, individually has been detected.

Further, the peptides allow the commercial test sensitivity, i.e. current gold reference standard for tubercular infection diagnosis (FIG. 10), to be enhanced. Both when panel estimated and directly tested within same well, 6 selected peptides allow Quantiferon-TB gold in-Tube to be enhanced from 75% to 89% (+14%) and from 71% to 83% (+13%), respectively, in subjects with active TB (see Table 4 and 5).

It is therefore a specific object of the present invention the use of at least 6 peptides, derived from *Mycobacterium tuberculosis* and comprising at least one T-cell epitope, in association with ESAT6 and CFP10 and, optionally with TB7.7, as biomarkers in an in vitro test for the detection of *Mycobacterium tuberculosis* infection in a subject, said peptides being chosen from the group consisting of: TAWITAVVPGLMV (SEQ ID NO:24), ELMARAAVLGSAH (SEQ ID NO:21), RPVRRVLLFWPSSGPAP (SEQ ID NO:70), GSVRQLPSVLKPPLITLRTLTLSG (SEQ ID NO:71), GEIIFISGRLNGaa (SEQ ID NO:13), AVIVRSELLTQYL (SEQ ID NO:22), LAWITAWPGLMV (SEQ ID NO:85), GEIIFISGRLNG (SEQ ID NO:86) or SALLRRLSTCPPES (SEQ ID NO:87). According to an embodiment of the present invention the peptides are the following six peptides: ELMARAAVLGSAH (SEQ ID NO:21), RPVRRVLLFWPSSGPAP (SEQ ID NO:70), GSVRQLPSVLKPPLITLRTLTLSG (SEQ ID NO:71), AVIVRSELLTQYL (SEQ ID NO:22), TAWITAVVPGLMV (SEQ ID NO:24) and GEIIFISGRLNGaa (SEQ ID NO:13). According to a further embodiment of the present invention, the peptides are the following six peptides: ELMARAAVLGSAH (SEQ ID NO:21), RPVRRVLLFVVPSSGPAP (SEQ ID NO:70), GSVRQLPSVLKPPLITLRTLTLSG (SEQ ID NO:71), AVIVRSELLTQYL (SEQ ID NO:22), LAWITAWPGLMV (SEQ ID NO:85) and GEIIFISGRLNG (SEQ ID NO:86). According to another embodiment of the present invention the peptides are all the following nine peptides: TAWITAVVPGLMV (SEQ ID NO:24), ELMARAAVLGSAH (SEQ ID NO:21), RPVRRVLLFVVPSSGPAP (SEQ ID NO:70), GSVRQLPSVLKPPLITLRTLTLSG (SEQ ID NO:71), GEIIFISGRLNGaa (SEQ ID NO:13), AVIVRSELLTQYL (SEQ ID NO:22), LAWITAWPGLMV (SEQ ID NO:85), GEIIFISGRLNG (SEQ ID NO:86) and SALLRRLSTCPPES (SEQ ID NO:87).

The present invention concerns also the use of at least one peptide, derived from *Mycobacterium tuberculosis* and comprising at least one T-cell epitope, in association with ESAT6 and CFP10 and, optionally, with TB7.7, as biomarker in an in vitro test for the detection of *Mycobacterium tuberculosis* infection in a subject, said peptide being chosen from the group consisting of: TAWITAVVPGLMV (SEQ ID NO:24), ELMARAAVLGSAH (SEQ ID NO:21), RPVRRVLLFVVPSSGPAP (SEQ ID NO:70), GSVRQLPSVLKPPLITLRTLTLSG (SEQ ID NO:71), GEIIFISGRLNGaa (SEQ ID NO:13), AVIVRSELLTQYL (SEQ ID NO:22), LAWITAWPGLMV (SEQ ID NO:85), GEIIFISGRLNG (SEQ ID NO:86) or SALLRRLSTCPPES (SEQ ID NO: 87). Particularly said at least one peptide can be LAWITAWPGLMV (SEQ ID NO:85) or TAWITAVVPGLMV (SEQ ID NO:24).

It is further object of the present invention a method for in vitro diagnosing infection by a *Mycobacterium tuberculosis* in a subject, said method comprising incubating a blood sample comprising lymphocytes from said subject in the presence of at least six peptides, derived from *Mycobacterium tuberculosis* and comprising at least one T-cell epitope, in association with ESAT6 and CFP10 and, optionally with TB7.7, for a time and under conditions sufficient to stimulate the lymphocytes to produce an effector molecule, wherein the presence or level of the effector molecule is indicative of the lymphocytes derived from a subject infected with or prior exposed to the *Mycobacterium* species, said at least six peptides being chosen from the group consisting of TAWITAVVPGLMV (SEQ ID NO:24), ELMARAAVLGSAH (SEQ ID NO:21), RPVRRVLLFVVPSSGPAP (SEQ ID NO:70), GSVRQLPSVLKPPLITLRTLTLSG (SEQ ID NO:71), GEIIFISGRLNGaa (SEQ ID NO:13), AVIVRSELLTQYL (SEQ ID NO:22), LAWITAWPGLMV (SEQ ID NO:85), GEIIFISGRLNG (SEQ ID NO:86) or SALLRRLSTCPPES (SEQ ID NO:87).

According to an embodiment of the method of the present invention, the peptides are the following six peptides: ELMARAAVLGSAH (SEQ ID NO:21), RPVRRVLL-FVVPSSGPAP (SEQ ID NO:70), GSVRQLPSVLKPPLITLRTLTLSG (SEQ ID NO:71), AVIVRSELLTQYL (SEQ ID NO:22), TAWITAVVPGLMV (SEQ ID NO:24) and GEIIFISGRLNGaa (SEQ ID NO:13). According to a further embodiment of the method of the present invention, the peptides are the following six peptides: ELMARAAVLGSAH (SEQ ID NO:21), RPVRRVLL-FVVPSSGPAP (SEQ ID NO:70), GSVRQLPSVLKPPLITLRTLTLSG (SEQ ID NO:71), AVIVRSELLTQYL (SEQ ID NO:22), LAWITAWPGLMV (SEQ ID NO:85) and GEIIFISGRLNG (SEQ ID NO:86). According to anther embodiment, the peptides are all the following nine peptides: TAWITAVVPGLMV (SEQ ID NO:24), ELMARAAVLGSAH (SEQ ID NO:21), RPVRRVLL-FVVPSSGPAP (SEQ ID NO:70), GSVRQLPSVLKPPLITLRTLTLSG (SEQ ID NO:71), GEIIFISGRLNGaa (SEQ ID NO:13), AVIVRSELLTQYL (SEQ ID NO:22), LAWITAWPGLMV (SEQ ID NO:85), GEIIFISGRLNG (SEQ ID NO:86) and SALLRRLSTCPPES (SEQ ID NO:87).

It is an object of the present invention a method for in vitro diagnosing infection by a *Mycobacterium tuberculosis* in a subject, said method comprising incubating a blood sample comprising lymphocytes from said subject in the presence of at least one peptide, derived from *Mycobacterium tuberculosis* and comprising at least one T-cell epitope, in association with ESAT6 and CFP10 and, optionally, with TB7.7, for a time and under conditions sufficient to stimulate the lymphocytes to produce an effector molecule, wherein the presence or level of the effector molecule is indicative of the lymphocytes derived from a subject infected with or prior exposed to the *Mycobacterium* species, said at least one peptide being chosen from the group consisting of TAWITAVVPGLMV (SEQ ID NO:24), ELMARAAVLGSAH (SEQ ID NO:21), RPVRRVLLFVVPSSGPAP (SEQ ID NO:70), GSVRQLPSVLKPPLITLRTLTLSG (SEQ ID NO:71), GEIIFISGRLNGaa (SEQ ID NO:13), AVIVRSELLTQYL (SEQ ID NO:22), LAWITAWPGLMV (SEQ ID NO:85), GEIIFISGRLNG (SEQ ID NO:86) or SALLRRLSTCPPES (SEQ ID NO:87). For example, said at least one peptide can be LAWITAWPGLMV (SEQ ID NO:85) or TAWITAVVPGLMV (SEQ ID NO:24).

It is further object of the present invention a method for the in vitro diagnosis of infection by *Mycobacterium tuberculosis* in a subject, said method including incubating a blood sample comprising lymphocytes from the subject with ESAT6 and CFP10, and optionally with TB7.7, and measuring release of interferon-γ by the lymphocytes, said method being characterized in that the incubation is carried out further in the presence of at least six peptides chosen from the group consisting of TAWITAVVPGLMV (SEQ ID NO:24), ELMARAAVLGSAH (SEQ ID NO:21), RPVRRVLLFVVPSSGPAP (SEQ ID NO:70), GSVRQLPSVLKPPLITLRTLTLSG (SEQ ID NO:71), GEIIFISGRLNGaa (SEQ ID NO:13), AVIVRSELLTQYL (SEQ ID NO:22), LAWITAWPGLMV (SEQ ID NO:85), GEIIFISGRLNG (SEQ ID NO:86) or SALLRRLSTCPPES (SEQ ID NO:87),
wherein the level of sensitivity and/or selectivity for the detection of *Mycobacterium tuberculosis* is higher compared to the sensitivity and/or selected using ESAT6 and CFP10, optionally with TB7.7. According to an embodiment of the present invention, the peptides are the following six peptides: ELMARAAVLGSAH (SEQ ID NO:21), RPVRRVLLFVVPSSGPAP (SEQ ID NO:70), GSVRQLPSVLKPPLITLRTLTLSG (SEQ ID NO:71), AVIVRSELLTQYL (SEQ ID NO:22), TAWITAVVPGLMV (SEQ ID NO:24) and GEIIFISGRLNGaa (SEQ ID NO:13). According to a further embodiment the peptides are the following six peptides: ELMARAAVLGSAH (SEQ ID NO:21), RPVRRVLLFVVPSSGPAP (SEQ ID NO:70), GSVRQLPSVLKPPLITLRTLTLSG (SEQ ID NO:71), AVIVRSELLTQYL (SEQ ID NO:22), LAWITAWPGLMV (SEQ ID NO:85) and GEIIFISGRLNG (SEQ ID NO:86). According to another embodiment the peptides are all the following nine peptides: TAWITAVVPGLMV (SEQ ID NO:24), ELMARAAVLGSAH (SEQ ID NO:21), RPVRRVLLFVVPSSGPAP (SEQ ID NO:70), GSVRQLPSVLKPPLITLRTLTLSG (SEQ ID NO:71), GEIIFISGRLNGaa (SEQ ID NO:13), AVIVRSELLTQYL (SEQ ID NO:22), LAWITAWPGLMV (SEQ ID NO:85), GEIIFISGRLNG (SEQ ID NO:86) and SALLRRLSTCPPES (SEQ ID NO:87).

The present invention concerns also a method for the in vitro diagnosis of infection by *Mycobacterium tuberculosis* in a subject, said method including incubating a blood sample comprising lymphocytes from the subject with ESAT6 and CFP10, and optionally with TB7.7, and measuring release of interferon-γ by the lymphocytes, said method being characterized in that the incubation is carried out further in the presence of at least one peptide chosen from the group consisting of TAWITAVVPGLMV (SEQ ID NO:24), ELMARAAVLGSAH (SEQ ID NO:21), RPVRRVLLFVVPSSGPAP (SEQ ID NO:70), GSVRQLPSVLKPPLITLRTLTLSG (SEQ ID NO:71), GEIIFISGRLNGaa (SEQ ID NO:13), AVIVRSELLTQYL (SEQ ID NO:22), LAWITAWPGLMV (SEQ ID NO:85), GEIIFISGRLNG (SEQ ID NO:86) or SALLRRLSTCPPES (SEQ ID NO:87).
wherein the level of sensitivity and/or selectivity for the detection of *Mycobacterium tuberculosis* is higher compared to the sensitivity and/or selected using ESAT6 and CFP10, optionally with TB7.7. Said at least one peptide can be LAWITAWPGLMV (SEQ ID NO:85) or TAWITAVVPGLMV (SEQ ID NO:24).

It is further object of the present invention the use of at least one biomarker selected from the list consisting of:
(i) a protein selected from Rv0023, Rv0182c, Rv0290, Rv0601c, Rv0647c, Rv0724A, Rv0890c, Rv1251c, Rv1398c, Rv1478, Rv1497, Rv1575, Rv1578c, Rv1899c, Rv2137c, Rv2333c, Rv2548, Rv2557, Rv2816c, Rv2990, Rv3094c, Rv3107c, Rv3188, Rv3239c, Rv3296, Rv3425, Rv3446c, Rv3479, Rv3482c, Rv3780, derived from a *Mycobacterium* species or related organism and comprising at least one T-cell epitope;
(ii) an homolog of the protein as defined in (i) having an amino acid sequence with at least 80% similarity in comparison to one of said protein after optimal alignment; and
(iii) a peptide fragment of the protein as defined in (i) or (ii) having a T-cell epitope or a chemical analog thereof;
in an in vitro test for the detection of *Mycobacterium* infection in a subject, i.e. an human or non human animal subject.

The *Mycobacterium* species can be selected from *M. tuberculosis, M. bovis, M. bovis* BCG, *M. africanum, M. canetti, M. caprae, M. microti, M. pinnipedii, M. avium, M. avium paratuberculosis, M. avium silvaticum, M. avium "hominissuis", M. colombiense, M. asiaticum, M. gordonae, M. gastri, M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. africanum, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. intermedium, M. abscessus, M. chelonae, M. bolletii, M. fortuitum, M. fortuitum* subsp. *acetamidolyticum, M. boenickei, M. peregrinum, M. porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smegmatis, M. goodii, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psy-* chrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense and M. tokaiense. Preferably, the Mycobacterium species is Mycobacterium tuberculosis.

According to the above use, the peptide fragment as defined in (iii) can comprise or consist of an amino acid sequence selected from TAWITAWPGLMV (SEQ ID NO:24), AVIVRSELLTQYL (SEQ ID NO:22), GSVRQLPSVLKPPLITLRTLTLSG (SEQ ID NO:71), RPVRRVLLFVVPSSGPAP (SEQ ID NO:70), GEIIFISGRLNGaa (SEQ ID NO:13), ELMARAAVLGSAH (SEQ ID NO:21), LAWITAWPGLMV (SEQ ID NO:85), GEIIFISGRLNG (SEQ ID NO:86), SALLRRLSTCPPES (SEQ ID NO:87).

The above use can further comprise the use of one or more Mycobacterium protein or peptide fragment thereof or chemical analog derived therefrom selected from ESAT6, CFP10, TB7.7 and PPD.

It is further object of the present invention the use of at least one biomarker selected from the list consisting of:

(i) a protein selected from Rv0023, Rv0182c, Rv0290, Rv0601c, Rv0647c, Rv0724A, Rv0890c, Rv1251c, Rv1398c, Rv1478, Rv1497, Rv1575, Rv1578c, Rv1899c, Rv2137c, Rv2333c, Rv2548, Rv2557, Rv2816c, Rv2990, Rv3094c, Rv3107c, Rv3188, Rv3239c, Rv3296, Rv3425, Rv3446c, Rv3479, Rv3482c, Rv3780, derived from a Mycobacterium species or related organism and comprising at least one T-cell epitope;

(ii) an homolog of the protein as defined in (i) having an amino acid sequence with at least 80% similarity to one of said protein after optimal alignment; and (iii) a peptide fragment of the protein as defined in (i) or (ii) having a T-cell epitope or a chemical analog thereof; and (iv) a Mycobacterium derived protein or fragment thereof or chemical analog thereof selected from the list consisting of:
  (a) ESAT;
  (b) CFP10;
  (c) TB7.7; and
  (d) PPD;
in an in vitro test for the detection of Mycobacterium infection in a subject i.e. an human or a non-human animal subject.

The Mycobacterium species can be selected from M. tuberculosis, M. bovis, M. bovis BCG, M. africanum, M. canetti, M. caprae, M. microti, M. pinnipedii, M. avium, M. avium paratuberculosis, M. avium silvaticum, M. avium "hominissuis", M. colombiense, M. asiaticum, M. gordonae, M. gastri, M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. africanum, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. intermedium, M. abscessus, M. chelonae, M. bolletii, M. fortuitum, M. fortuitum subsp. acetamidolyticum, M. boenickei, M. peregrinum, M. porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smegmatis, M. goodii, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense and M. tokaiense. Preferably, the Mycobacterium species is Mycobacterium tuberculosis.

According to the above use, the peptide fragment as defined in (iii) can comprise or consist of an amino acid sequence selected from TAWITAWPGLMV (SEQ ID NO:24), AVIVRSELLTQYL (SEQ ID NO:22), GSVRQLPSVLKPPLITLRTLTLSG (SEQ ID NO:71), RPVRRVLLFVVPSSGPAP (SEQ ID NO:70), GEIIFISGRLNGaa (SEQ ID NO:13), ELMARAAVLGSAH (SEQ ID NO:21), LAWITAWPGLMV (SEQ ID NO:85), GEIIFISGRLNG (SEQ ID NO:86), SALLRRLSTCPPES (SEQ ID NO:87).

It is a further object of the present invention the use of at least one nucleic acid molecule encoding for a biomarker selected from the list consisting of:

(i) a protein selected from Rv0023, Rv0182c, Rv0290, Rv0601c, Rv0647c, Rv0724A, Rv0890c, Rv1251c, Rv1398c, Rv1478, Rv1497, Rv1575, Rv1578c, Rv1899c, Rv2137c, Rv2333c, Rv2548, Rv2557, Rv2816c, Rv2990, Rv3094c, Rv3107c, Rv3188, Rv3239c, Rv3296, Rv3425, Rv3446c, Rv3479, Rv3482c, Rv3780, derived from a Mycobacterium species or related organism and comprising at least one T-cell epitope;

(ii) an homolog of the protein as defined in (i) having an amino acid sequence with at least 80% similarity to one of said protein after optimal alignment; and (iii) a peptide fragment of the protein as defined in (i) or (ii) having a T-cell epitope or chemical analog thereof;
in an in vitro test for the detection of Mycobacterium infection in a subject i.e. an human or a non-human animal subject.

The Mycobacterium species is selected from M. tuberculosis, M. bovis, M. bovis BCG, M. africanum, M. canetti, M. caprae, M. microti, M. pinnipedii, M. avium, M. avium paratuberculosis, M. avium silvaticum, M. avium "hominissuis", M. colombiense, M. asiaticum, M. gordonae, M. gastri, M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. africanum, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. intermedium, M. abscessus, M. chelonae, M. bolletii, M. fortuitum, M. fortuitum subsp. acetamidolyticum, M. boenickei, M. peregrinum, M. porcinum, M. senegalense, M. septicum, M. neworleansense, M. houstonense, M. mucogenicum, M. mageritense, M. brisba-

*nense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smegmatis, M. goodii, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense* and *M. tokaiense*. Preferably, the *Mycobacterium* species is *Mycobacterium tuberculosis.*

According to the above use, the peptide fragment in (iii) can comprise or consist of an amino acid sequence selected from TAWITAWPGLMV (SEQ ID NO:24), AVIVRSELLTQYL (SEQ ID NO:22), GSVRQLPSVLKPPLITLRTLTLSG (SEQ ID NO:71), RPVRRVLLFVVPSSGPAP (SEQ ID NO:70), GEIIFISGRLNGaa (SEQ ID NO:13), ELMARAAVLGSAH (SEQ ID NO:21), LAWITAWPGLMV (SEQ ID NO:85), GEIIFISGRLNG (SEQ ID NO:86), SALLRRLSTCPPES (SEQ ID NO:87). Said use can further comprise use of a nucleic acid molecule encoding for a *Mycobacterium* protein or peptide fragment derived therefrom selected from ESAT6, CFP10, TB7.7 and PPD or an homolog thereof.

It is further object of the present invention, an isolated protein selected from the list consisting of Rv0023, Rv0182c, Rv0290, Rv0601c, Rv0647c, Rv0724A, Rv0890c, Rv1251c, Rv1398c, Rv1478, Rv1497, Rv1575, Rv1578c, Rv1899c, Rv2137c, Rv2333c, Rv2548, Rv2557, Rv2816c, Rv2990, Rv3094c, Rv3107c, Rv3188, Rv3239c, Rv3296, Rv3425, Rv3446c, Rv3479, Rv3482c, Rv3780, derived from a *Mycobacterium* species and comprising a T-cell epitope. The isolated peptide of the protein according to the invention can comprise a T-cell epitope or a chemical analog thereof. The isolated peptide according can comprise or consist of an amino acid sequence selected from TAWITAWPGLMV (SEQ ID NO:24), AVIVRSELLTQYL (SEQ ID NO:22), GSVRQLPSVLKPPLITLRTLTLSG (SEQ ID NO:71), RPVRRVLLFVVPSSGPAP (SEQ ID NO:70), GEIIFISGRLNGaa (SEQ ID NO:13), ELMARAAVLGSAH (SEQ ID NO:21), LAWITAWPGLMV (SEQ ID NO:85), GEIIFISGRLNG (SEQ ID NO:86), SALLRRLSTCPPES (SEQ ID NO:87).

It is further object of the present invention an isolated nucleic acid molecule encoding for the above mentioned protein or peptide according to the present invention.

The present invention concerns a vector comprising the above mentioned nucleic acid molecule, and isolated cell comprising said vector.

It is a further object of the present invention a kit comprising a container, said container comprising the above mentioned at least one protein or at least one a peptide or at least one a nucleic acid molecule.

The present invention concerns a method for in vitro diagnosing infection by a *Mycobacterium* species in a subject, said method comprising incubating a blood sample comprising lymphocytes from said subject in the presence of at least one biomarker selected from the list consisting of:

(i) a protein selected from Rv0023, Rv0182c, Rv0290, Rv0601c, Rv0647c, Rv0724A, Rv0890c, Rv1251c, Rv1398c, Rv1478, Rv1497, Rv1575, Rv1578c, Rv1899c, Rv2137c, Rv2333c, Rv2548, Rv2557, Rv2816c, Rv2990, Rv3094c, Rv3107c, Rv3188, Rv3239c, Rv3296, Rv3425, Rv3446c, Rv3479, Rv3482c, Rv3780, derived from a *Mycobacterium* species or related organism and comprising at least one T-cell epitope;

(ii) an homolog of the protein as defined in (i) having an amino acid sequence with at least 80% similarity to one of said protein after optimal alignment; and (iii) a peptide fragment of the protein as defined in (i) or (ii) having a T-cell epitope or a chemical analog thereof;

for a time and under conditions sufficient to stimulate the lymphocytes to produce an effector molecule, wherein the presence or level of the effector molecule is indicative of the lymphocytes derived from a subject infected with or prior exposed to the *Mycobacterium* species. The subject can be an human or a non-human animal. The incubation between blood and biomarker can occur in a test-tube, optionally in the presence of heparin, in the presence of an added carbohydrate. According to an embodiment of the present invention, the incubation can occur further in the presence of a *Mycobacterium* protein or peptide fragment thereof or chemical analog thereof derived therefrom selected from ESAT6, CFP10, TB7.7 and PPD or mixture thereof. The *Mycobacterium* species is selected from *M. tuberculosis, M. bovis, M. bovis* BCG, *M. africanum, M. canetti, M. caprae, M. microti, M. pinnipedii, M. avium, M. avium paratuberculosis, M. avium silvaticum, M. avium* "hominissuis", *M. colombiense, M. asiaticum, M. gordonae, M. gastri, M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. africanum, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. intermedium, M. abscessus, M. chelonae, M. bolletii, M. fortuitum, M. fortuitum* subsp. *acetamidolyticum, M. boenickei, M. peregrinum, M. porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smegmatis, M. goodii, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense* and *M. tokaiense*. Preferably, the *Mycobacterium* species is *Mycobacterium tuberculosis*.

According to the above-mentioned method of the invention, the peptide as defined in (iii) comprises or consists of an amino acid sequence selected from TAWITAWPGLMV (SEQ ID NO:24), AVIVRSELLTQYL (SEQ ID NO:22), GSVRQLPSVLKPPLITLRTLTLSG (SEQ ID NO:71), RPVRRVLLFVVPSSGPAP (SEQ ID NO:70), GEIIFISGRLNGaa (SEQ ID NO:13), ELMARAAVLGSAH (SEQ ID NO:21), LAWITAWPGLMV (SEQ ID NO:85), GEII-FISGRLNG (SEQ ID NO:86), SALLRRLSTCPPES (SEQ ID NO:87). The effector molecule can be selected from interferon-γ, a cytokine, an interleukin and TNF-α, preferably interferon-γ.

It is a further object of the present invention an isolated antibody specific for the protein or peptide defined above according.

The invention concerns also a method for the in vitro diagnosis of infection by *Mycobacterium tuberculosis* in a subject, said method including incubating a blood sample comprising lymphocytes from the subject with one or more of ESAT6, CFP10, TB7.7 and/or PPD and measuring release of interferon-γ by the lymphocytes, said method being characterized in that the incubation is carried out further in the presence of at least one biomarker selected from:

(i) a protein selected from Rv0023, Rv0182c, Rv0290, Rv0601c, Rv0647c, Rv0724A, Rv0890c, Rv1251c, Rv1398c, Rv1478, Rv1497, Rv1575, Rv1578c, Rv1899c, Rv2137c, Rv2333c, Rv2548, Rv2557, Rv2816c, Rv2990, Rv3094c, Rv3107c, Rv3188, Rv3239c, Rv3296, Rv3425, Rv3446c, Rv3479, Rv3482c, Rv3780, derived from a *Mycobacterium* species or related organism and comprising at least one T-cell epitope;

(ii) an homolog of the protein as defined in (i) having an amino acid sequence with at least 80% similarity to one of said protein after optimal alignment; and (iii) a peptide fragment of the protein as defined in (i) or (ii) having a T-cell epitope or chemical analog thereof; wherein the level of sensitivity and/or selectivity for the detection of *Mycobacterium tuberculosis* is higher compared to the sensitivity and/or selected using one or more of ESAT6, CFP10, TB7.7 and/or PPD alone.

In addition, the present invention concerns vaccine for the treatment or prophylaxis of infection by a *Mycobacterium* species, said vaccine comprising or consisting of at least one agent selected from the list consisting of:

(i) a protein selected from Rv0023, Rv0182c, Rv0290, Rv0601c, Rv0647c, Rv0724A, Rv0890c, Rv1251c, Rv1398c, Rv1478, Rv1497, Rv1575, Rv1578c, Rv1899c, Rv2137c, Rv2333c, Rv2548, Rv2557, Rv2816c, Rv2990, Rv3094c, Rv3107c, Rv3188, Rv3239c, Rv3296, Rv3425, Rv3446c, Rv3479, Rv3482c, Rv3780, derived from a *Mycobacterium* species or related organism and comprising at least one T-cell epitope;

(ii) an homolog of the protein as defined in (i) having an amino acid sequence with at least 80% similarity to one of said protein after optimal alignment; and (iii) a peptide fragment of the protein as defined in (i) or (ii) having a T-cell epitope or chemical analog thereof; and one or more pharmaceutically acceptable adjuvants, carriers, excipients and/or diluents.

According to the vaccine of the present invention, the *Mycobacterium* species is selected from *M. tuberculosis, M. bovis, M. bovis* BCG, *M. africanum, M. canetti, M. caprae, M. microti, M. pinnipedii, M. avium, M. avium paratuberculosis, M. avium silvaticum, M. avium* "hominissuis", *M. colombiense, M. asiaticum, M. gordonae, M. gastri, M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. africanum, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. intermedium, M. abscessus, M. chelonae, M. bolletii, M. fortuitum, M. fortuitum* subsp. *acetamidolyticum, M. boenickei, M. peregrinum, M. porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smegmatis, M. goodii, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense* and *M. tokaiense*. Preferably, the *Mycobacterium* species is *Mycobacterium tuberculosis*.

Vaccine of the present invention can be use in human or non-human animal subject. The peptide as defined in (iii) can comprise or consist of an amino acid sequence selected from TAWITAVVPGLMV (SEQ ID NO:24), AVIVRSELLTQYL (SEQ ID NO:22), GSVRQLPSVLKPPLITLRTLTLSG (SEQ ID NO:71), RPVRRVLLFVVPSSGPAP (SEQ ID NO:70), GEIIFISGRLNGaa (SEQ ID NO:13), ELMARAAVLGSAH (SEQ ID NO:21), LAWITAWPGLMV (SEQ ID NO:85), GEIIFISGRLNG (SEQ ID NO:86), SALLRRLSTCPPES (SEQ ID NO:87). Therefore, the present invention concerns vaccine as define above for use in the prevention of infection by *Mycobacterium* species.

It is further object of the present invention, at least one agent selected from the list consisting of:

(i) a protein selected from Rv0023, Rv0182c, Rv0290, Rv0601c, Rv0647c, Rv0724A, Rv0890c, Rv1251c, Rv1398c, Rv1478, Rv1497, Rv1575, Rv1578c, Rv1899c, Rv2137c, Rv2333c, Rv2548, Rv2557, Rv2816c, Rv2990, Rv3094c, Rv3107c, Rv3188, Rv3239c, Rv3296, Rv3425, Rv3446c, Rv3479, Rv3482c, Rv3780, derived from a *Mycobacterium* species or related organism and comprising at least one T-cell epitope;

(ii) an homolog of the protein as defined in (i) having an amino acid sequence with at least 80% similarity to one of said protein after optimal alignment; and (iii) a peptide fragment of the protein as defined in (i) or (ii) having a T-cell epitope or a chemical analog thereof; for use in the treatment or prevention of infection by *Mycobacterium* species.

The present invention further concerns a method for in vitro assessing the capacity for a subject to mount a cell-mediated immune response, said method comprising contacting a sample comprising T-lymphocytes sensitized to *Mycobacterium* species or antigens or proteins comprising T-lymphocyte epitopes derived therefrom with at least one agent selected from:

(i) a protein selected from Rv0023, Rv0182c, Rv0290, Rv0601c, Rv0647c, Rv0724A, Rv0890c, Rv1251c, Rv1398c, Rv1478, Rv1497, Rv1575, Rv1578c, Rv1899c, Rv2137c, Rv2333c, Rv2548, Rv2557, Rv2816c, Rv2990, Rv3094c, Rv3107c, Rv3188, Rv3239c, Rv3296, Rv3425, Rv3446c, Rv3479, Rv3482c, Rv3780, derived from a *Mycobacterium* species or related organism and comprising at least one T-cell epitope;

(ii) an homolog of the protein as defined in (i) having an amino acid sequence with at least 80% similarity to one of said protein after optimal alignment; and (iii) a peptide fragment of the protein as defined in (i) or (ii) having a T-cell epitope or a chemical analog thereof;

for a time and under conditions sufficient to stimulate the lymphocytes to produce an effector molecule, wherein the presence or level of the effector molecule is indicative of the subject's capacity to mount a cell-mediated immune response.

The present invention now will be described by an illustrative, but not limitative way, according to preferred embodiments thereof, with particular reference to enclosed drawings wherein:

FIG. 1. Analysis of IFN-gamma production as PPD response comparing four subject populations: a. first test pulmonary TB patients; b. healthy contacts, TB exposed, PPD positive; c. healthy controls, professionally TB exposed, Quantiferon positive; d. negative controls, Quantiferon negative, BCG vaccinated.

Figure 2:
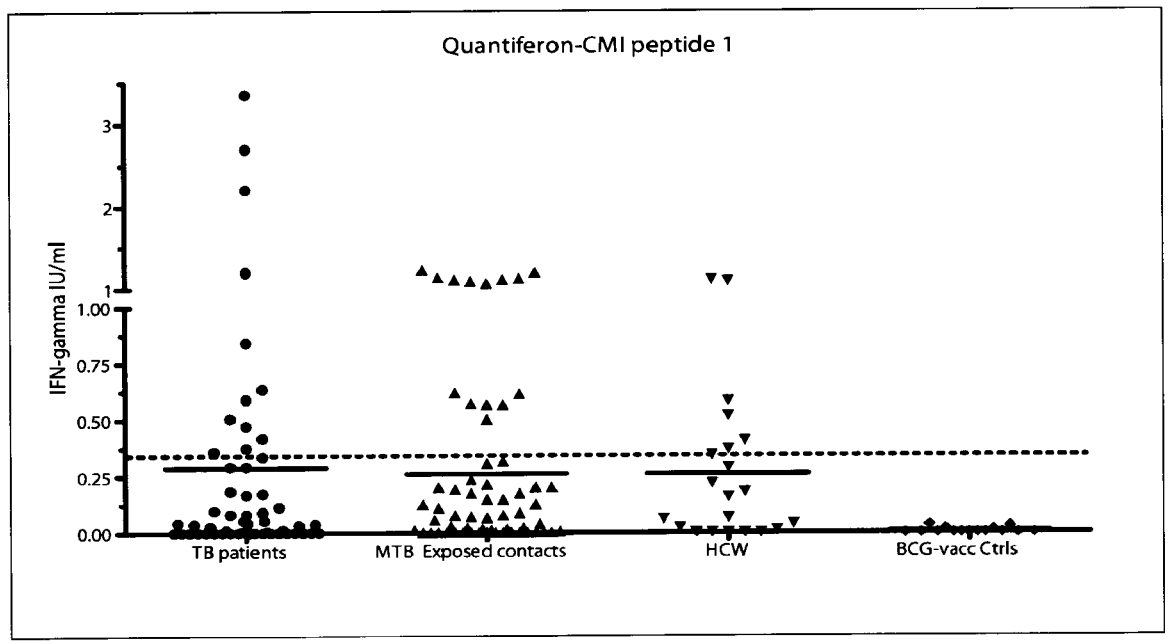

FIG. 2. Analysis of IFN-gamma production as TAWITAVVPGLMV (SEQ ID NOT 24) peptide response from 4 tested subject groups.

Figure 3:
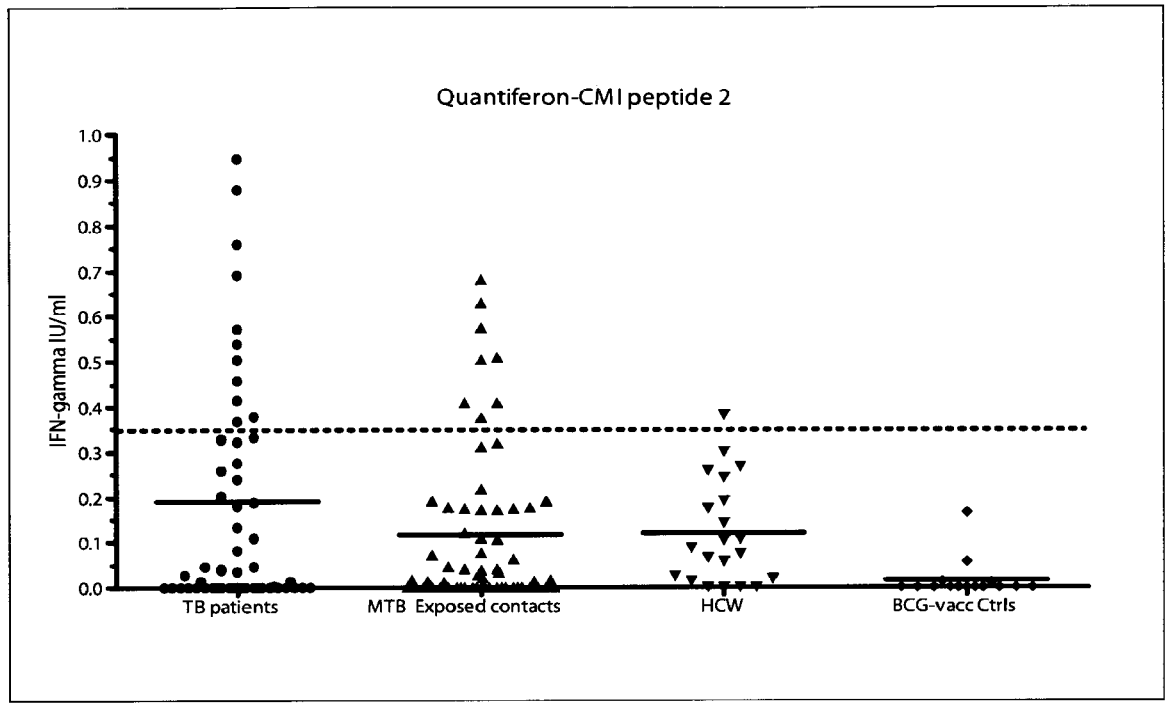

FIG. 3. Analysis of IFN-gamma production as AVIVRSELLTQYL (SEQ ID NO 22) peptide response from 4 tested subject groups.

Figure 4:
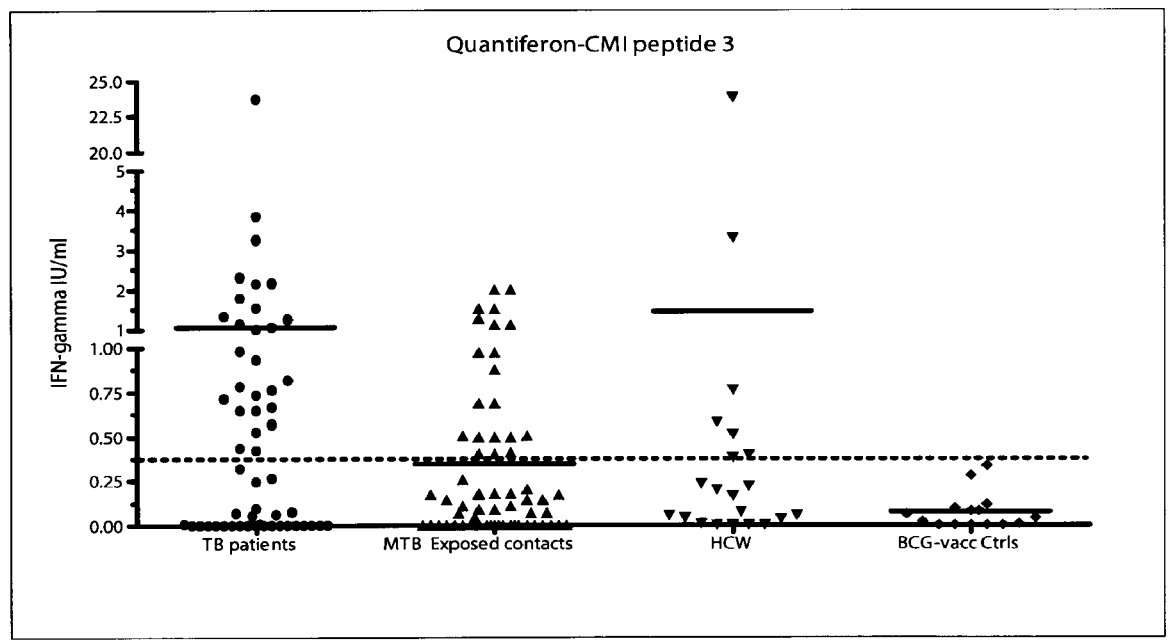

FIG. 4. Analysis of IFN-gamma production as GSVRQLPSVLKPPLITLRTLTLSG (SEQ ID NO 71) peptide response from 4 tested subject groups.

Figure 5:
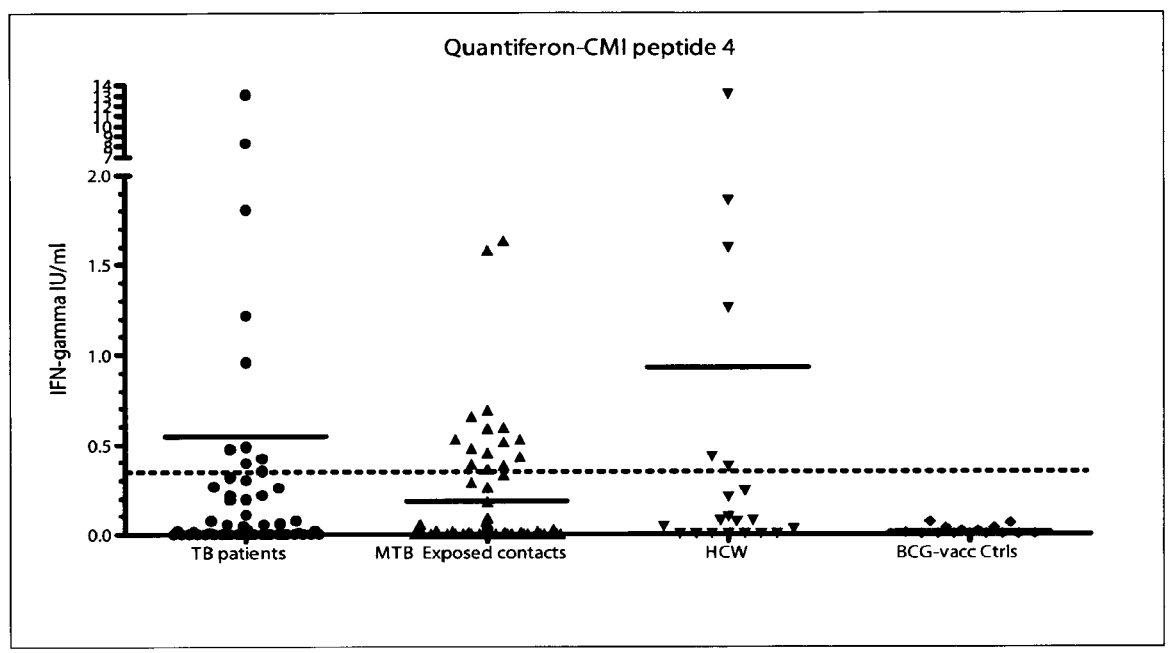

FIG. 5. Analysis of IFN-gamma production as RPVRRVLLFVVPSSGPAP (SEQ ID NO 70) peptide response from 4 tested subject groups.

Figure 6:
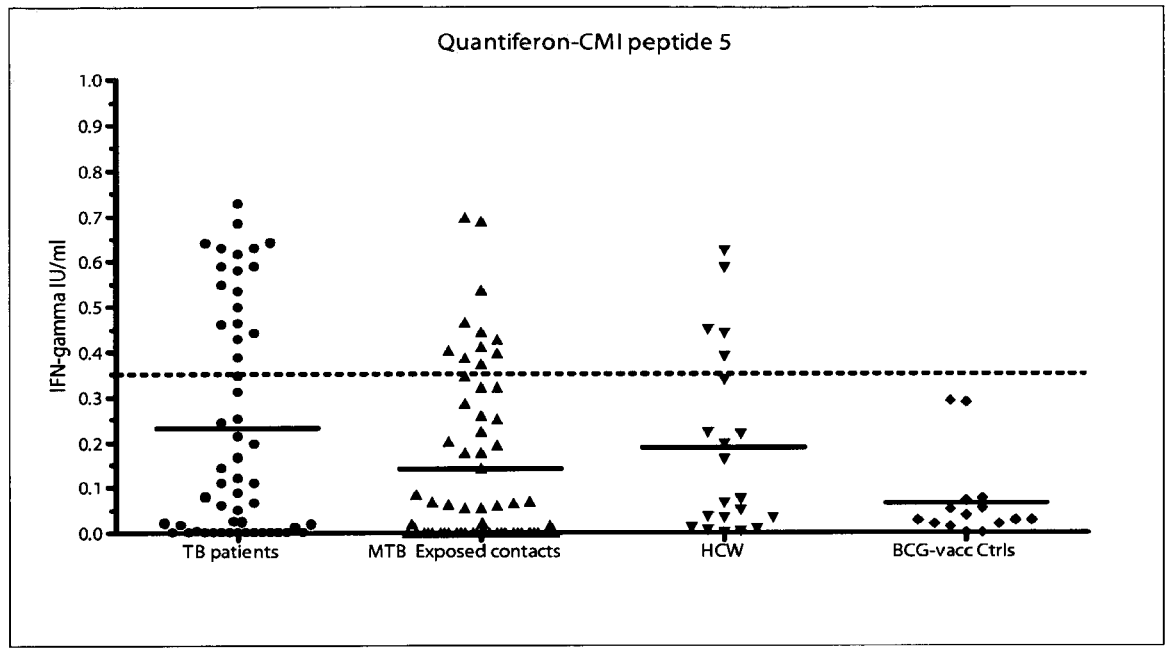

FIG. 6. Analysis of IFN-gamma production as GEIIFISGRLNGaa (SEQ ID NO 13) peptide response of tested samples.

Figure 7:
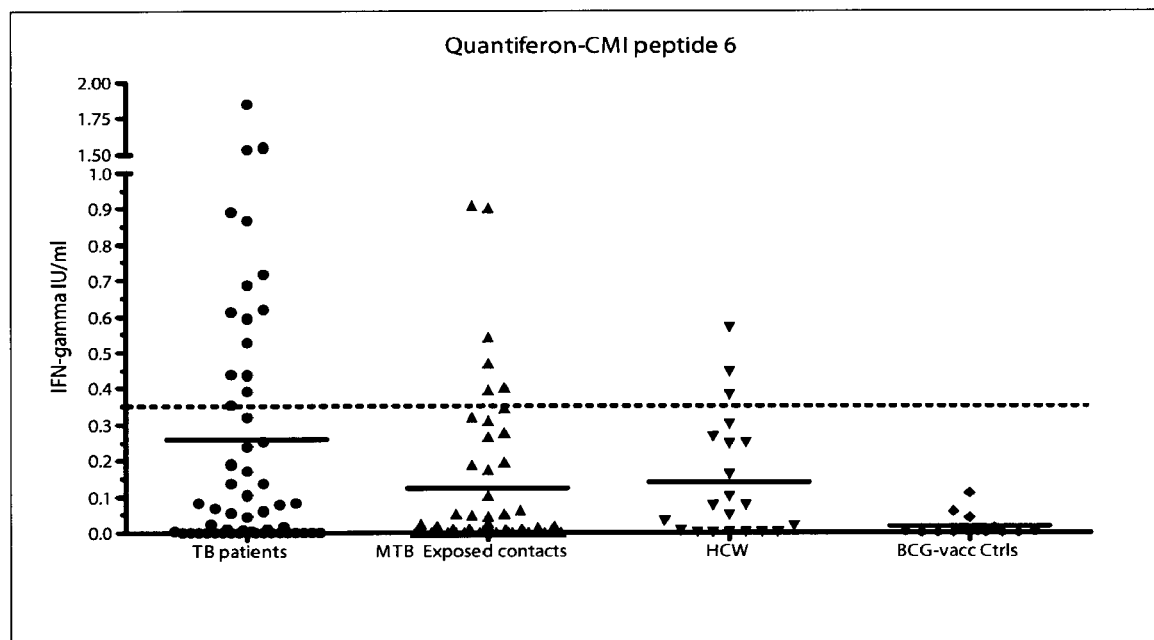

FIG. 7. Analysis of IFN-gamma production as ELMARAAVLGSAH (SEQ ID NO 21) peptide response of tested samples.

Figure 8:
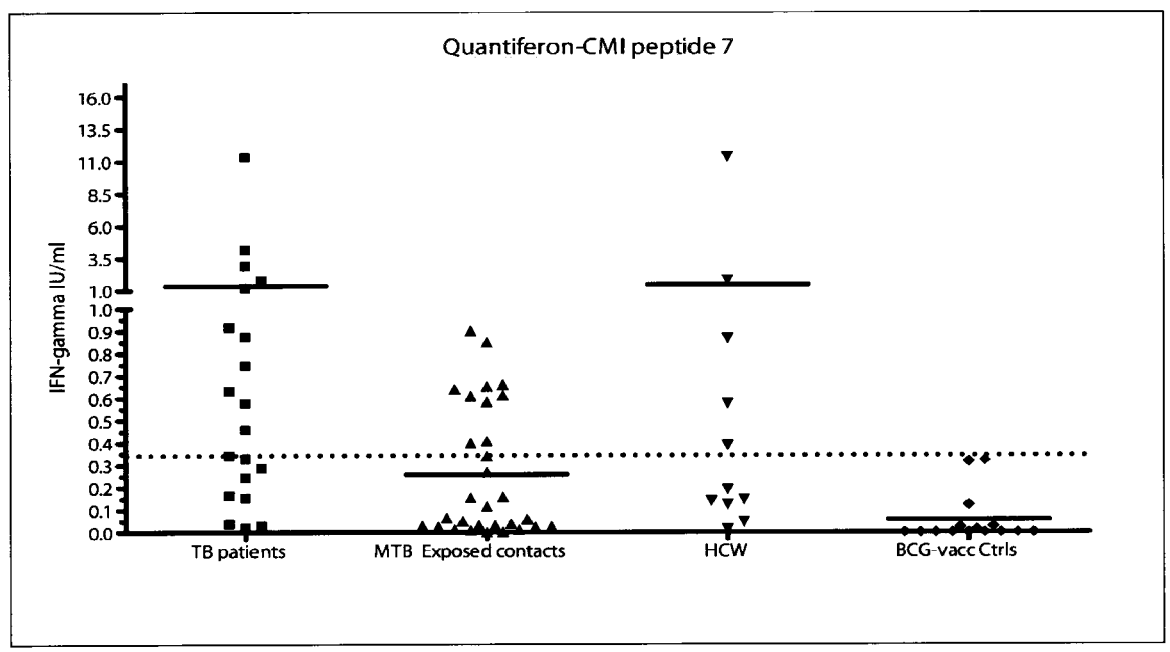

FIG. 8. Analysis of IFN-gamma production as ESAT6 (QQWNFAGIEAAASAIQGNVTSIHSL—SEQ ID NO:84) response of tested samples.

Figure 9:
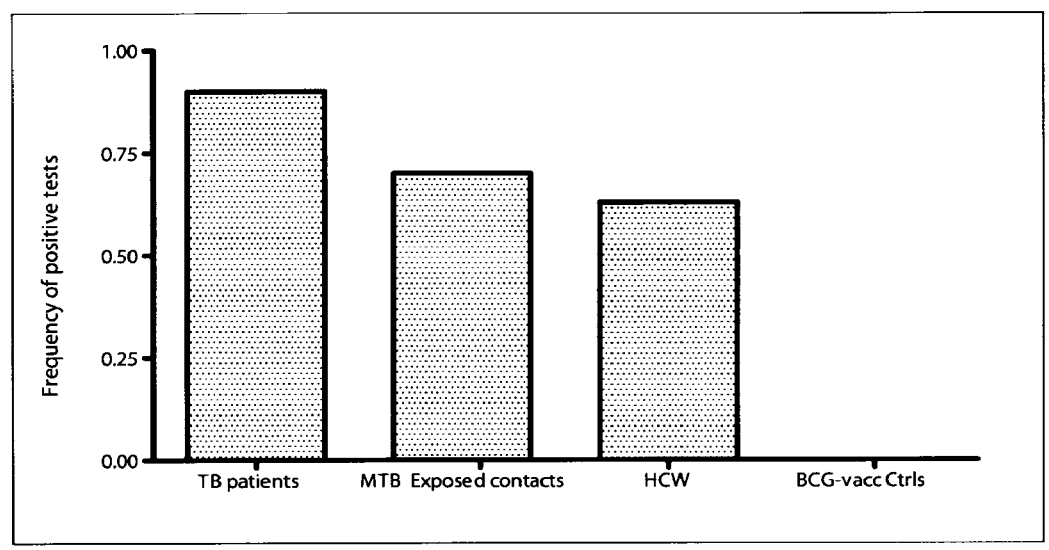

FIG. 9. Frequency of positive tests using only SEQ ID NO:24, 21, 71, 70, 13, 22 six peptides.

Figure 10:
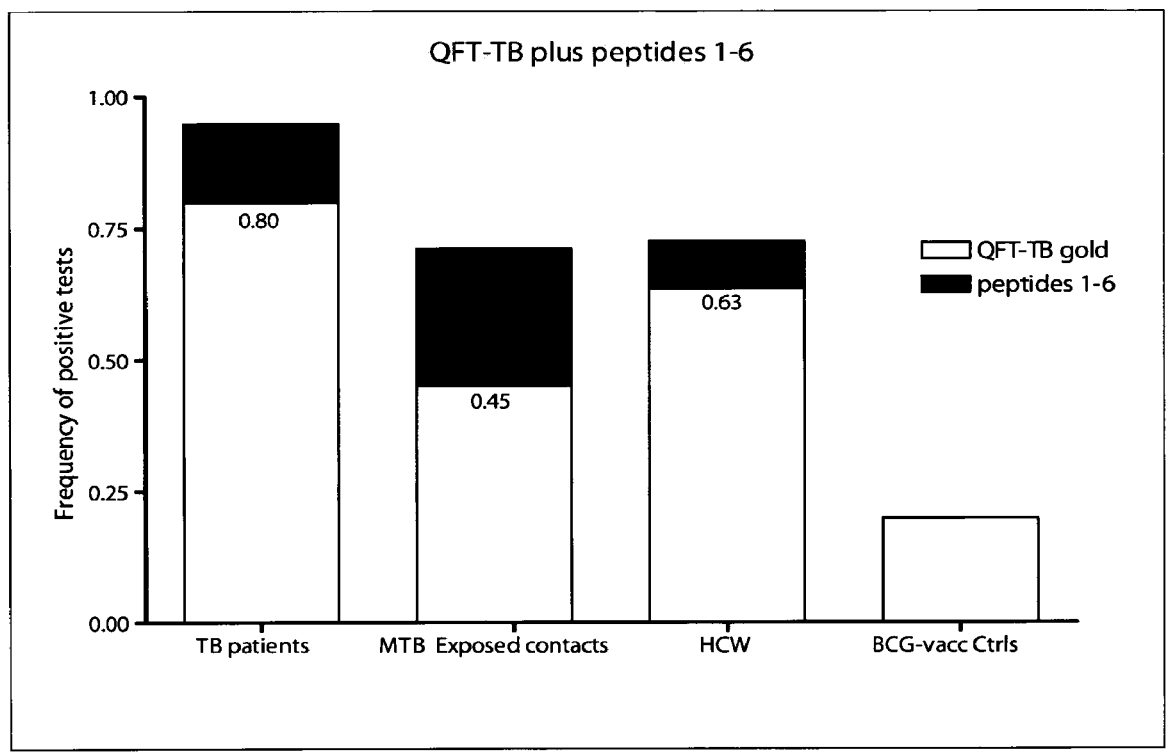

FIG. 10. Sensitivity increase of Quantiferon TB-plus commercial used test after SEQ ID NO: 24, 21, 70, 71, 13, 22 peptide addition thereto.

Figure 11:
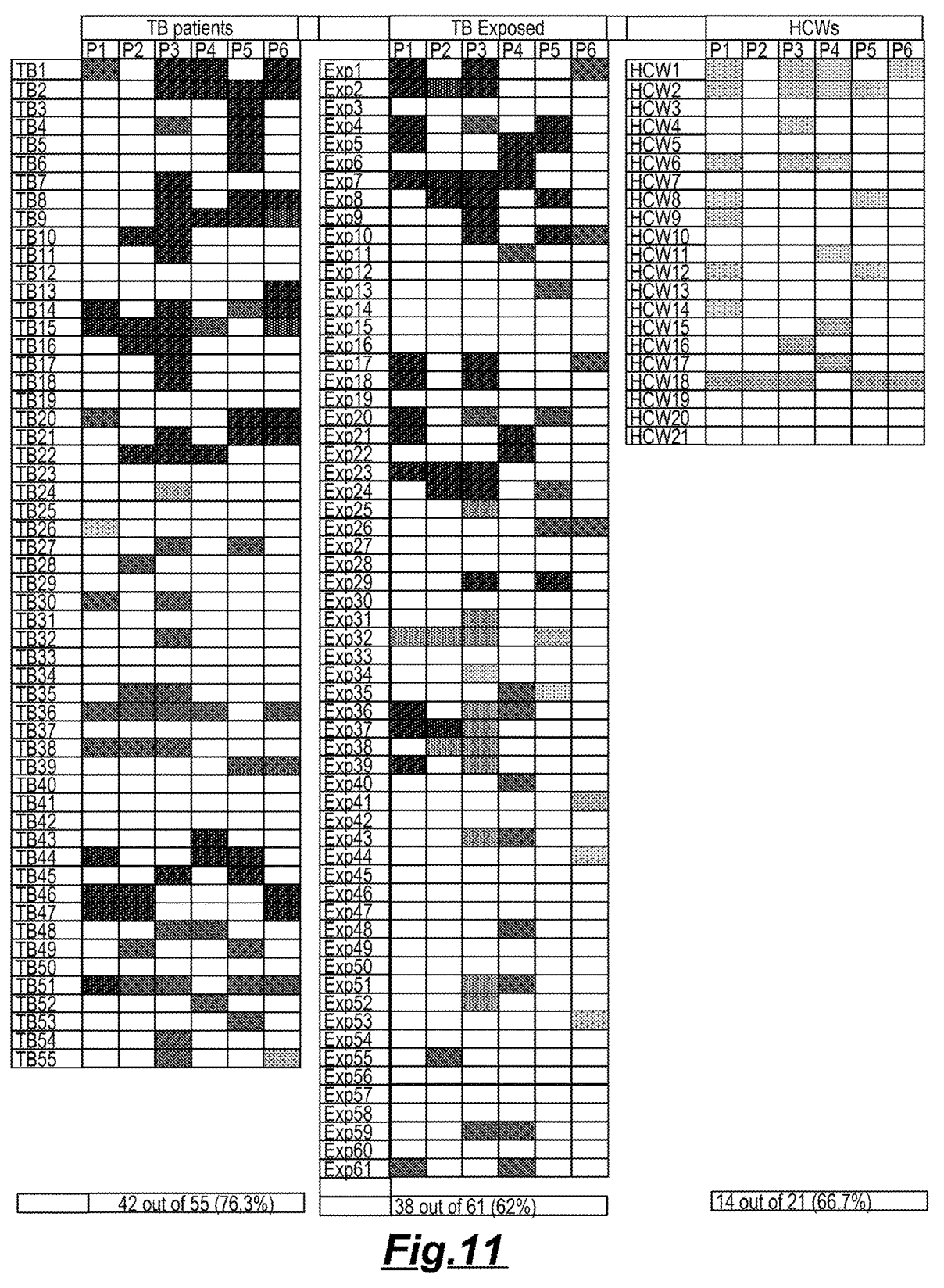

FIG. 11. Combination use of 1-6 peptides, which allow in panel a 76.3%, 62% and 66.7%, compared to 55%, 33% and 45.5% sensitivity obtained using RD1 (ESAT6) multiepitope peptide, for TB+ subjects, PPD+ esposed contacts and HCWs, respectively, to be obtained.

EXAMPLE 1

Identification of *M. tuberculosis* Expressed Proteins in Human Infected Macrophages from Both Vitro and Ex Vivo Analyzed Biological Samples Materials and Methods ELISPOT Immunodiagnostic Test The global procedure for test carrying out demands for: 96 well plates (MAIPS45, Millipore, Sunnyvale, Calif., USA); primary antibody (IFN-gamma coating monoclonal, M-700A, Pierce-Endogen Inc, Rockford, USA); biotynilated antibody (M-701B, Pierce-Endogen Inc); streptavidin-HRP (Pierce-Endogen); substrate (AEC Staining kit, Sigma); stimulus (peptides, PHA and other antigens) at ready to use concentration.

ELISPOT procedure is carried out according to the following step:

Coating: treatment of a 96 well plate using 5 μg/mL sterile phosphate buffer (PBS) solution of primary antibody delivered at 100 μL/well; coat the plate and incubate at 4° C. for 20 hours; wash the plate 4 times using 200 μL/well of sterile PBS, at final washing eliminate excess liquid by tapping plate on adsorbent paper.

Blocking: addition of 200 μL/well of "blocking solution" [sterile PBS containing 10% fetal calf serum (FCS)], in order to prevent not specific protein binding; plate incubation for 2 hours at room temp.; "blocking solution" suction.

Cell Preparation and Incubation 1. isolation of mononucleated cells (PBMC) from venous blood (7 ml with EDTA) by density gradient centrifugation (Ficoll-Hypaque, Pharmacia; Uppsala; Sweden), using a quick method based on the use of filtering tubes for leucocytes separation (LeucoSep™, ARNIKA, Milan). After two washings with PBS (phosphate buffered saline) 1×, the pellet is resuspended in complete medium (RPMI 1640 containing HEPES 25 mM, 10% v/v FCS, 2 mM L-Glutamine, 10 U/mL penicillin/streptomycin)) in order to have $2\times10^5$ cells in 100 μL.

2. add 100 μL/well of cellular suspension together with 100 μL of different stimula;

3. incubate the plate for 40 hours at 37° C. in incubator at 5% $CO_2$;

4. remove the cells;

5. wash the plate 4 times with 200 μL/well of PBS and 4 times with 200 μL/well of "Wash buffer" [PBS/0.05% Tween 20 (Sigma)];

6. at the final washing eliminate the excess liquid by tapping the plate on absorbent paper.

Incubation with Biotinilated Antibody

100 μl/well of biotinilated antibody diluted in PBS/4% bovine serum albumin (fraction V, Sigma) at concentration of 1 μg/ml have been delivered. Then the plate has been incubated for 100 minutes at 37° C. in incubator at 5% $CO_2$; the plate has been washed 4 times with "Wash buffer". At final washing excess liquid has been eliminated by tapping plate on adsorbent paper.

Detection

For the detection 100 μl/well of "Streptavidin-HRP" 1:1000 diluted in "Wash buffer". The plate has been incubated for 30 minutes at room temp. in the dark, then washed 4 times with "Wash buffer". At final washing excess liquid has been eliminated by tapping plate on adsorbent paper. 100 μL/well of substrate have been delivered. In parallel as a control for enzyme-substrate reaction occurrence 100 μl of as prepared substrate with 100 μl of "diluted Streptavidin-HRP" has been incubated for few minutes. If the reaction is successful the substrate turns out from light brown to pink colour.

Finally the plate has been incubated for 10-20 minutes at room temp. in the dark. The substrate has been discarded, the plate washed with water eliminating excess and air dried for 20 hours.

ELISA tests for the identification of human and animal IFN-gamma in whole blood samples stimulated with selected peptides and proteins (CMI test protocol).

Results

The authors have identified the group of *M. tuberculosis* expressed proteins in human infected macrophages from both in vitro and ex vivo analyzed biological samples. *M.* tuberculosis gene expressions in three different growth environments have been compared: synthetic medium (Sauton's), monocyte-derived-human macrophage (MDM) infected in culture with *M. tuberculosis*, alveolar macrophage (AM) from bronchoalveolar lavage (BAL) samples of pulmonary TB affected patients before the antibiotic therapy.

From thus obtained 9 groups of genes, first 100 proteins, according to a combination criteria (immunogenicity, tubercular Complex specificity, etc), have been selected. From these 100 proteins, again a 30 protein group has been selected, for which a positive response in immunological tests on TB patient whole blood had been obtained.

TABLE 1

| Rv | In vivo modulation | Amino acid sequence ID (UNIPROT) | Already tested peptides |
|---|---|---|---|
| Rv0023 | B, E | P67704 | EMWDIRNRGVIPAGALPRVR (SEQ ID NO: 1) |
| Rv0182c | E | O07426 | AKFRSVRVVVITGSVTAAPVRVSETLRRLI (SEQ ID NO: 2), ESVRLAFVAALQH (SEQ ID NO: 3) |
| Rv0290 | D | O86362 | GLLITIRSPRSGIA (SEQ ID NO: 4), AQLLWQLPLLSIG (SEQ ID NO: 5) |
| Rv0601c | C, E | O07777 | ADLVRELVTILPIVLVIAAVAAYLLSR (SEQ ID NO: 6) AAYLLSRAALRPVDRIRAAA (SEQ ID NO: 7) TTLNTMLTRLQRALAHEQQF (SEQ ID NO: 8) DLFVSIDPDHLRRILTAVLDN (SEQ ID NO: 9) SGLGLAIVAALTTTHGG (SEQ ID NO: 10) |
| Rv0647c | E | P96936 | GRLPRKGPWQQKVIKELPQ (SEQ ID NO: 11), GKIVVLMGAVGTMKPETQAA (SEQ ID NO: 12) |
| Rv0724A | B | Q79FX1 | GEIIFISGRLNGaa (SEQ ID NO: 13) |
| Rv0890c | C, E | Q10550 | ARVRSMSPLEIAD (SEQ ID NO: 14), EQILFRRLAPFVGGF (SEQ ID NO: 15), AALVRALTACGCSS (SEQ ID NO: 16), DKWTLCQILYWRGVGTCISGD (SEQ ID NO: 17), TKVLGLYTQAQVLAYCG (SEQ ID NO: 18), DQVTMHQVLMAQLALAGG (SEQ ID NO: 19), EGVRLLGAAAALRQQTRQVRFK (SEQ ID NO: 20) |
| Rv1251c | C, E | O50466 | ELMARAAVLGSAH (SEQ ID NO: 21), AVIVRSELLTQYL (SEQ ID NO: 22) |
| Rv1398c | D | P64835 | GTLRHLDPPVRRSGGREQHL (SEQ ID NO: 23) |
| Rv1478 | E | O53169 | TAWITAVVPGLMV (SEQ ID NO: 24) |
| Rv1497 | C, E | P71778 | APMVFSATKGMTA (SEQ ID NO: 25), TCAMRRLAHRFSGG (SEQ ID NO: 26) |
| Rv1575 | C, E | O06615 | SVVRRKQTLLSAQ (SEQ ID NO: 27) |
| Rv1578c | E | O06612 | GVVHRNPAVTVAE (SEQ ID NO: 28) |
| Rv1899c | D | O07733 | PGVVATHAVRTLGTTGSRAIGL (SEQ ID NO: 29), PQWRRARVRLCGRWWRRSNTTRGAS (SEQ ID NO: 30), ARLMVGAVRRHRPGSLQR (SEQ ID NO: 31) |
| Rv2137c | D | O06238 | aaMRNMKSTSHE (SEQ ID NO: 32) |
| Rv2333c | E | P71879 | QTIVMLWTAAVGCA (SEQ ID NO: 33), LCMLMLGLLMLIFSEHRSS (SEQ ID NO: 34), SALVLVGLGLCGSGVALCLT (SEQ ID NO: 35) |
| Rv2548 | A, E | P95005 | SELVRFELLAGVRESE (SEQ ID NO: 36), VDYLIAATAIVVDA (SEQ ID NO: 37) |
| Rv2557 | A, E | P65003 | QGIEYYKSSVLPQIE (SEQ ID NO: 38), EGWIVYARSTTIQAQS (SEQ ID NO: 39), TRRMYSNYGF (SEQ ID NO: 40) |
| Rv2816c | A | P71637 | FGYRVQESAFEAMLTKGQLAKLV (SEQ ID NO: 41), DNIRIYKIRGVAAVTFYGRGRLVSAE (SEQ ID NO: 42) |
| Rv2990 | E | O53239 | RSYILRAGISSLFRYIEGVHGER (SEQ ID NO: 43), SAMRPQDRLLVGNWVDDSLL (SEQ ID NO: 44), LYLVGLEPYVQFE (SEQ ID NO: 45), AGFRILEARRFPI (SEQ ID NO: 46), IRYRARYVNGQLNMCLARI (SEQ ID NO: 47) |
| Rv3094c | E | O05773 | ALLVAYLPARSREEMF (SEQ ID NO: 48), NRLRLAATHAVRT (SEQ ID NO: 49), APLQRRFRDAFTATAHFQVNE (SEQ ID NO: 50), SRELPGRVLLDQPADVSM (SEQ ID NO: 51) |
| Rv3107c | A, E | O05784 | EPVVTVDVTAMSAVLEID (SEQ ID NO: 52) |
| Rv3188 | C, E | O53334 | AVIQVSDRAVRGWRTGDIRPERY (SEQ ID NO: 53) |

TABLE 1-continued

| Rv | In vivo modulation | Amino acid sequence ID (UNIPROT) | Already tested peptides |
|---|---|---|---|
| Rv3239c | C, E | O05884 | PDLRGALLLAVTLGLVT (SEQ ID NO: 54), PDWGWLSVATVGSFLA (SEQ ID NO: 55), GAVLGVAVMVILIGKPEHGTA (SEQ ID NO: 56), AAICFIAVAVAAAVL (SEQ ID NO: 57), TKLVRLTKAQFDEIA (SEQ ID NO: 58), ADLVLAGPAASREH (SEQ ID NO: 59), YAYEYFIRHNPLSDYA (SEQ ID NO: 60), FPVRGLVRGRRTLTLLEA (SEQ ID NO: 61) |
| Rv3296 | A, E | P96901 | EVLRILRRRSLAALRA (SEQ ID NO: 62), RVILHSPYGLRVHGPLAL (SEQ ID NO: 63) |
| Rv3425 | E | Q50703 | AAWVINGLANAYNDT (SEQ ID NO: 64), DQYRARNVAVMNAYVSWTRSALSDLPR (SEQ ID NO: 65), SDLLADAVERYLQWLSKSSSQLKHA (SEQ ID NO: 66) |
| Rv3446c | C, E | O06263 | GPVVVHPSWWSAA (SEQ ID NO: 67), ITAVVLIDVPSTVAGA (SEQ ID NO: 68), AAVVRHGATTLQRP (SEQ ID NO: 69) |
| Rv3479 | C, E | O06342 | RPVRRVLLFVVPSSGPAP (SEQ ID NO: 70), GSVRQLPSVLKPPLITLRTLTLSG (SEQ ID NO: 71), SALLRRLSTCPPES (SEQ ID N: 87) |
| Rv3482c | E | O06345 | GAVLRLVVRFAEPLPPSP (SEQ ID NO: 72), AGYLLTYTIANNGKEFAEL (SEQ ID NO: 73) |
| Rv3780 | D | P65091 | aaVRKRMVIGLSTGSDDD (SEQ ID NO: 74) |
| Cons FS | | | ALLLRDVLQWKSAEVADAIG (SEQ ID NO: 75), NSLLQRARSQLQTVRPSAADRLSAA (SEQ ID NO: 76) |
| Cons PE_PGRS | | | MSWVMVSPELVVAAAADLAG (SEQ ID NO: 77) AAFYAQFVQALTSGGAY (SEQ ID NO: 78) |
| Cons REG | | | ALLVRMPTSLPAVA (SEQ ID NO: 79) |
| Cons CW | | | SRLRTHVRPDAPLVPLALRVDGLRSRW (SEQ ID NO: 80) AAVLTMLGVAGYGW (SEQ ID NO: 81) GLFMIFLDALIVNVALPDIQR (SEQ ID NO: 82) SWVVASYSLGMAVFIMSAGTLADLL (SEQ ID NO: 83) |

Legend of Modulation:
A: up-regulated in AM vs MDM;
B: always expressed in AM and MDM;
C: up-regulated in MDM vs AM;
D: up-regulated in Sauton vs MDM and/or AM;
E: up-regulated in MDM and/or AM vs Sauton's After an ulterior selection initially 43 peptides from 4 groups of subjects: Pulmonary TB before antibiotic therapy (n=13), recently exposed healthy contacts (TB patient relations) PPD+(n=8); long TB patient exposed healthy contacts (professional exposure of hospital workers) PPD+(n=5); BCG vaccinated negative controls, PPD- (n=4), have been designed, synthesized and tested.

Then 6 most sensible and specific peptides have been selected (see table 2) and the study has been repeated using an extended subject sample (see tables 3-4 and FIGS. 1-7).

Table 2 reports MTB selected genes, peptides selected for T CD4+ cell assay and corresponding identification number thereof, respectively.

TABLE 2

| N° | Peptide | Gene | In vivo modulation |
|---|---|---|---|
| SEQ ID NO: 24 | TAWITAVVPGLMV | Consensus VIR (Rv1478) | Induced in AM and MDM vs Sauton's |
| SEQ ID NO: 22 | AVIVRSELLTQYL | Rv1251c | Induced in MDM vs Sauton's |
| SEQ ID NO: 71 | GSVRQLPSVLKPPLITLR TLTLSG | Rv3479 | Induced in MDM vs Sauton's |
| SEQ ID NO: 70 | RPVRRVLLFVVPSSGPAP | Rv3479 | Induced in MDM vs Sauton's |
| SEQ ID NO: 13 | GEIIFISGRLNGaa | Rv0724A | Expressed in AM and MDM |
| SEQ ID NO: 21 | ELMARAAVLGSAH | Rv1251c | Induced in MDM vs Sauton's |

TABLE 3

| | Microbiologically checked TB patients (before therapy start) | Recently MTB exposed subjects | Sanitary workers | BCG-vaccinated controls |
|---|---|---|---|---|
| Examined subject number | 58 | 63 | 21 | 15 |
| Anergic subjects (mitogene low response or no response to all stimula) | 3/58 | 2/63 | 0/21 | 0/15 |
| Quantiferon TB-Gold in-Tube | 41/55 | 25/61 | 11/21 | 3/15 |
| PPD | 55/55 | 61/61 | 21/21 | 15/15 |
| ESAT-6 control peptide | 28/55 | 17/61 | 7/21 | 0/15 |
| Peptide #1 (Seq ID N°:24) | 12/55 | 14/61 | 6/21 | 0/15 |
| Peptide #2 (Seq ID N°:22) | 11/55 | 8/61 | 1/21 | 0/15 |
| Peptide #3 (Seq ID N°:71) | 27/55 | 20/61 | 7/21 | 0/15 |
| Peptide #4 (Seq ID N°:70) | 10/55 | 13/61 | 6/21 | 0/15 |
| Peptide #5 (Seq ID N°:13) | 18/55 | 11/61 | 5/21 | 0/15 |

TABLE 3-continued

| | Microbiologically checked TB patients (before therapy start) | Recently MTB exposed subjects | Sanitary workers | BCG-vaccinated controls |
|---|---|---|---|---|
| Peptide #6 (Seq ID N° :21) | 14/55 | 6/61 | 3/21 | 0/15 |

TABLE 4

| | Microbiologically checked TB patients (before therapy start) | Recently MTB exposed subjects | Sanitary workers | BCG-vaccinated controls |
|---|---|---|---|---|
| Examined subject number | 58 | 63 | 21 | 15 |
| Anergic subjects (mitogene low response or no response to all stimula) | 3/58 | 2/63 | 0/21 | 0/15 |
| Quantiferon TB-Gold in-Tube | 41/55 | 25/61 | 11/21 | 3/15 |
| Panel 1-6 peptides | 40/55 | 30/61 | 11/21 | 0/15 |
| QFT Gold +30 panel 1-6 peptides | 49/55 | 34/61 | 13/21 | 3/15 |

TABLE 5

| | Microbiologically checked TB patients (before therapy start) | Recently MTB exposed subjects | Sanitary workers | BCG-vaccinated controls |
|---|---|---|---|---|
| Examined subject number | 38 | 32 | 10 | 10 |
| Anergic | 3 | 1 | 0 | 0 |
| 1-6 peptides (in pool) | 22/35 | 10/31 | 4/10 | 1/10 |
| QFT Gold | 25/35 | 11/31 | 4/10 | 2/10 |
| QFT Gold + 1-6 peptides in same well | 29/35 | 13/31 | 5/10 | 2/10 |

Results obtained with said six peptides and peptide belonging to ESAT6 protein, i.e. a highly immunogenic protein occurring in both above mentioned commercial kits, have been compared.

MTB genes observed as induced, both in course of human macrophage infection and/or in alveolar macrophage samples from active pulmonary TB patients, are indicated in the following list:

Genes always expressed during intracellular replication in MDM and AM: Rv0724A.

Genes induced in AM and/or MDM vs Sauton's medium culture: Rv1251c, Rv1478 and Rv3479.

Two groups of MTB genes share probable role in the survival inside human host cell (both primary macrophages from healthy in vitro infected donors and TB patient alveolar macrophages) resulting in design thereof as MTB intracellular survival bio-markers, whereas MTB virulence definition is just based on the pathogen ability to invade, survive and replicate within the host cell.

Moreover, the authors of the present invention have designed peptides of some gene groups belonging to same metabolic category, in order to find "consensus" protein sequences for said categories. The research is based on the assumption that functional domains of similar function exploiting proteins occurring in various bacterial species, are conserved. In order to find these conserved motifs the sequence multiple alignment (PSSM), using PSI-BLAST (Position Specific Iterated Basic Local Alignment Search Tool, http://www.ncbi.nlm.nih.gov/BLAST), is generated. After the sequences with higher similarity grades with the inserted sequence has been detected, it is possible to select the proteins suitable to contribute to the generation of the profile used for the successive data bank search; in this way the number of the sequences contributing to the generation of the profile is different for the different sequence positions.

A multi-alignment allows structurally and functionally important, because extremely conserved, residues to be detected and said residues as a whole will constitute the "consensus" sequence or sequences for each MTB protein functional group.

Therefore proteins (induced or repressed in human macrophage) of metabolic functional groups (for example regulatory proteins, lipid metabolism involved proteins, etc.) detected as "modulated" by M. tuberculosis during infection course, have been analyzed for search of conserved sequences. Using PSI-BLAST sequence various multiple alignments, from which we have reached the best "consensus" sequences for the peptide synthesis, have been obtained.

The peptides derived from selected proteins have been synthesized and used for the detection and quantification of MTB specific T CD4+ lymphocytes using detection system for IFN-γ producing cells both with ELISPOT technique and with TB diagnosis high sensitivity ELISA assay, Quantiferon TB-Plus and Quantiferon CMI. This technique allows the frequency of T cells producing a determined cytokine (for example, IFN-γ) as a response to a specific antigenic stimulus suggesting that the immune system of treated subjects has been able to evoke an immune response towards said peptides when infectious agent (MTB) encoding for the same occurs, to be quantified. The second technique allows total IFN-gamma production resulting from specific T lymphocytes as a response to selected antigens, to be quantified.

Although this test does not represent the evidence of ability thereof to induce protection from MTB infection, the occurred detection of the presence of lymphocytes recognizing these peptides specifically and differently in MTB infected subjects or with active tuberculosis, is an index of their immunogenicity, indispensable minimal characteristic in order a vaccine and a diagnostic test to be proved effective. Further these peptides, alone or in addition to other mycobacterial antigens, allow a sensitive and specific test for TB diagnosis to be provided and the sensitivity of commercial test, i.e. current reference gold standard for the tubercular diagnosis, to be enhanced (FIG. 10). When panel evaluated and directly tested within same well, 6 selected peptides allow Quantiferon TB gold in-Tube response from 75% to 89% (+14%) and from 71% to 83% (+13%), respectively, for subjects with active TB, to be enhanced, without decreasing the assay specificity.

BIBLIOGRAPHY

1. E W Koneman, S D Allen, W M Janda, P. Schreckenberger, W C Winn. Color Atlas and Textbook of Diagnostic Microbiology. 5ª edizione. Lippincot, 1997
2. Menzies D, Pai M, Comstock G. Ann Intern Med. 2007 Mar. 6; 146(5):340-54. Meta-analysis: new tests for the diagnosis of latent tuberculosis infection: areas of uncertainty and recommendations for research
3. Bellete B, Coberly J, Barnes G L, Ko C, Chaisson R E, Comstock G W, Bishai W R. Clin Infect Dis. 2002 34:1449-56.
4. Pai M, Gokhale K, Joshi R, Dogra S, Kalantri S, Mendiratta D K, Narang P, Daley C L, Granich R M, Mazurek G H, Reingold A L, Riley L W, Colford J M Jr. JAMA. 2005 293:2746-55.
5. Lalvani A, Pathan A A, Durkan H, Wilkinson K A, Whelan A, Deeks J J, Reece W H, Latif M, Pasvol G, Hill A V. Lancet. 2001; 357: 2017-21.
6. Centers for Disease Control and Prevention. MMWR Recomm Rep. 1997 Sep. 5; 46(RR-15):1-10.
7. Ulrichs T, Munk M E, Mollenkopf H, et al. Eur J Immunol 1998; 28:3949-3958.
8. Ravn P, Demissie A, Eguale T, et al. J Infect Dis 1999; 179:637-645.
9. Doherty T M, Demissie A, Olobo J, et al. J Clin Microbiol 2002; 40:704-706.
10. Lalvani A, Pathan A A, Durkan H, et al. Lancet 2001; 357:2017-2021.
11. Lalvani A, Nagvenkar P, Udwadia Z, et al. J Infect Dis 2001; 183:469-477.
12. Chapman A L, Munkanta M, Wilkinson K A, et al. AIDS 2002; 16:2285-2293.
13. Lalvani A, Pathan A A, McShane H, et al. Am J Respir Crit Care Med 2001; 163:824-828.
14. Pathan A A, Wilkinson K A, Klenerman P, et al. J Immunol 2001; 167:5217-5225.
15. LinksLawn S D, Bangani N, Vogt M, Bekker L G, Badri M, Ntobongwana M, Dockrell H M, Wilkinson R J, Wood R. Utility of interferon-γ ELISPOT assay responses in highly tuberculosis-exposed patients with advanced HIV infection in South Africa. BMC Infect Dis. 2007 Aug. 28; 7:99
16. De Groot A S, Bosma A, Chinai N, Frost J, Jesdale B M, Gonzalez M A, Martin W, Saint-Aubin C. Vaccine 2001, 19:4385-4395.
17. Brander C, Goulder P J R. Edited by Korber B T M, Brander C, Haynes B, Koup R A, Kuiken C, Moore J, Walker B, Watkins D. Los Alamos National Laboratory, Los Alamos, N. Mex. 2000; 11-13.

The invention claimed is:

1. A method for detecting a *Mycobacterium tuberculosis* infection in a test subject, comprising:
   (a) incubating in vitro a blood sample or a lavage sample that comprises lymphocytes from the test subject with at least one isolated protein or peptide that comprises at least one *Mycobacterium tuberculosis* T-cell epitope, said isolated protein or peptide being selected from:
      SEQ ID NO:1 (Rv0023), SEQ ID NOS:2-3 (Rv0182c) and SEQ ID NOS: 4-5 (Rv0290),
   wherein said step of incubating is for a time and under conditions sufficient to stimulate the lymphocytes to produce an effector molecule; and
   (b) detecting a test level of the effector molecule, wherein detection of a test level that is higher than a control level that is detected following incubation of control lymphocytes from a healthy control subject, indicates that the test subject is infected with, or has been previously exposed to, the *Mycobacterium tuberculosis*.

2. The method of claim 1 wherein the subject is a human or non-human animal and either or both of:
   (1) the isolated protein or peptide consists of an amino acid sequence selected from SEQ ID NO: 1, SEQ ID NO: 2, SEQ ID NO: 3, SEQ ID NO: 4 and SEQ ID NO: 5,
   (2) in the step of incubating there is present one or more *Mycobacterium* protein, selected from ESAT6, CFP10, TB7.7 and PPD, and the detected test level of the effector molecule is greater than a detectable effector molecule level that can be produced by said lymphocytes incubated only with said one or more *Mycobacterium* protein selected from ESAT6, CFP10, TB7.7 and PPD.

* * * * *